United States Patent
Rubin et al.

(10) Patent No.: US 9,458,213 B2
(45) Date of Patent: Oct. 4, 2016

(54) COMPOSITIONS AND METHODS FOR DIAGNOSING PROSTATE CANCER BASED ON DETECTION OF SLC45A3-ELK4 FUSION TRANSCRIPT

(75) Inventors: Mark A. Rubin, New York, NY (US); Dorothee Pflueger, Zurich (CH); David S. Rickman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 705 days.

(21) Appl. No.: 13/202,207

(22) PCT Filed: Feb. 19, 2010

(86) PCT No.: PCT/US2010/024748
§ 371 (c)(1),
(2), (4) Date: Aug. 18, 2011

(87) PCT Pub. No.: WO2010/096660
PCT Pub. Date: Aug. 26, 2010

(65) Prior Publication Data
US 2012/0039887 A1    Feb. 16, 2012

Related U.S. Application Data

(60) Provisional application No. 61/153,835, filed on Feb. 19, 2009.

(51) Int. Cl.
*C12Q 1/68* (2006.01)
*C07K 14/47* (2006.01)
*C12N 15/62* (2006.01)

(52) U.S. Cl.
CPC .......... *C07K 14/4748* (2013.01); *C12N 15/62* (2013.01); *C12Q 1/6886* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,582,908 B2 * | 6/2003 | Fodor et al. | 506/9 |
| 2007/0212702 A1 | 9/2007 | Tomlins et al. | |
| 2012/0015839 A1 * | 1/2012 | Chinnaiyan | 506/9 |

FOREIGN PATENT DOCUMENTS

| | | |
|---|---|---|
| WO | 2007/033187 A2 | 3/2007 |
| WO | 2010/081001 A2 | 7/2010 |

OTHER PUBLICATIONS

Pfluger, Master's Thesis, "Towards Understanding of Prostate Cancer Heterogeneity" Faculty of Medicine of Ulm University, Materprogram Molecular Medicine 2008, 58 pages.*
Pflueger et al. SLC45A3 is a common ETS Family Fusion Partner in Prostate Cancer, presented in poster session A of the AACR Special Conference on Jan. 21-24, 2009.*
Attard, G. et al., "Duplication of the fusion of TMPRSS2 to ERG sequences identifies fatal human prostate cancer" Oncogene (2007) pp. 253-263, vol. 27.
Cheville, J.C. et al., "Gene Panel Model Predictive of Outcome in Men at High-Risk of Systemic Progression and Death From Prostate Cancer After Radical Retropubic Prostatectomy" Journal of Clinical Oncology (2008) pp. 3930-3936, vol. 26.
Demichelis, F. et al., "TMPRSS2:ERG Gene Fusion Associated with Lethal Prostate Cancer in a Watchful Waiting Cohort" Oncogene (2007) pp. 4596-4599, vol. 26.
Helgeson, B.E. et al., "Characterization of TMPRSS2:ETV5 and SLC45A3:ETV5 Gene Fusions in Prostate Cancer" Cancer Research (2008) pp. 73-80, vol. 68.
McCarroll, S.A. et al., "Integrated Detection and Population-Genetic Analysis of SNPs and Copy Number Variation" Nature Genetics (Oct. 2008) pp. 1166-1174, vol. 40, No. 10.
Mosquera, J-M. et al., "Morphological Features of TMPRSS2-ERG Gene Fusion Prostate Cancer" Journal of Pathology (2007) pp. 91-101, vol. 212.
Perner, S. et al., "TMPRSS2:ERG Fusion-Associated Deletions Provide Insight into the Heterogeneity of Prostate Cancer" Cancer Research (Sep. 1, 2006) pp. 8337-8341, vol. 66, No. 17.
Setlur, S.R. et al., "Estrogen-Dependent Signaling in a Molecularly Distinct Subclass of Aggressive Prostate Cancer" J Natl Cancer Inst (2008) pp. 815-825, vol. 100.
Tomlins, S.A. et al., "TMPRSS2:ETV4 Gene Fusions Define a Third Molecular Subtype of Prostate Cancer" Cancer Research (2006) pp. 3396-3400, vol. 66.
Tomlins, S.A. et al., "Distinct Classes of Chromosomal Rearrangements Create Oncogenic ETS Gene Fusions in Prostate Cancer" Nature (Aug. 2, 2007) pp. 595-599, vol. 448.
Tomlins, S.A. et al., "Recurrent Fusion of TMPRSS2 and ETS Transcription Factor Genes in Prostate Cancer" Science (Oct. 28, 2005) pp. 644-648, vol. 310.
Wolf, M. et al., "High-Resolution Analysis of Gene Copy Number Alterations in Human Prostate Cancer Using CGH on cDNA Microarrays: Impact of Copy Number on Gene Expression" Neoplasia (May/Jun. 2004) pp. 240-247, vol. 6, No. 3.
Xu, J. et al., "Common Sequence Variants of the Macrophage Scavenger Receptor 1 Gene Are Associated with Prostate Cancer Risk" Am. J. Hum. Genet. (2003) pp. 208-212, vol. 72.
Yin, M. et al., "Diagnostic Utility of p501s (prostein) in Comparison to Prostate Specific Antigen (PSA) for the Detection of Metastatic Prostatic Adenocarcinoma" Diagnostic Pathology (2007) pp. 41, vol. 2.
Han et al., "A Fluorescence in situ Hybridization Screen for E26 Transformation-Specific Aberrations: Identification of DDX5-ETV4 Fusion Protein in Prostate Cancer" Cancer Research (Sep. 15, 2008) pp. 7629-7637, vol. 68, No. 18.
Makkonen, et al., "Identification of ETS-like Transcription Factor 4 as a Novel Androgen Receptor Target in Prostate Cancer Cells" Oncogene (May 12, 2008) pp. 4865-4876, vol. 27, No. 36.

(Continued)

*Primary Examiner* — Juliet Switzer
(74) *Attorney, Agent, or Firm* — Scully, Scott, Murphy & Presser, P.C.

(57) ABSTRACT

RNA transcripts representing a fusion of a human SLC45A3 nucleic acid and a human ELK4 nucleic acid that are associated with prostate cancer are described. Compositions and methods useful for detection of fusion transcripts of human SLC45A3 and ELK4 genetic sequences associated with cancer and useful for cancer therapy are provided.

3 Claims, 6 Drawing Sheets

(56) References Cited

OTHER PUBLICATIONS

Sun, et al., "TMPRSS2-ERG Fusion, a Common Genomic Alteration in Prostate Cancer Activates C-MYC and Abrogates Prostate Epithelial Differentiation" Oncogene (Jun. 9, 2008) pp. 5348-5353, vol. 27, No. 40.
Rickman, et al., "SLC45A3-ELK4 is a Novel and Frequent: Erythroblast Transformation-Specific Fusion Transcript in Prostate Cancer" Cancer Research (Mar. 17, 2009) pp. 2734-2738, vol. 69, No. 7.
Maher, et al., "Transcriptome Sequencing to Detect Gene Fusions in Cancer" Nature (Mar. 5, 2009) pp. 1-42, vol. 458, No. 7234.
International Search Report dated Nov. 11, 2010 issued in International Application No. PCT/US2010/024748.
Cheng, H. et al., "Novel Transcript Fusion SLC45A3-ELK4 Variants in Prostate Cancer" Annual Meetings (2010) pp. 184A, 814.
Supplementary European Search Report dated Sep. 5, 2012 issued in European Application No. EP 10 74 4361.
Tomlins, S.A. et al., "The Role of SPINK1 in ETS Rearrangement-Negative Prostate Cancers" Cancer Cell (Jun. 2008) pp. 519-528, vol. 13.
De Kok, J.B. et al., "DD3 (PCA3), a Very Sensitive and Specific Marker to Detect Prostate Tumors" Cancer Research (May 1, 2002) pp. 2695-2698, vol. 68.
Laxman, B. et al., "A First-Generation Multiplex Biomarker Analysis of Urine for the Early Detection of Prostate Cancer" Cancer Research (Feb. 1, 2008) pp. 645-649, vol. 68, No. 3.
Takahara, T. et al., "Delay in Synthesis of the 3' Splice Site Promotes Trans-Splicing of the Preceding 5' Splice Site" Molecular Cell (Apr. 15, 2005) pp. 245-251, vol. 18.
Pradet-Balade, B. et al., "An Endogenous Hybrid mRNA Encodes TWE-PRIL, a Functional Cell Surface TWEAK-APRIL Fusion Protein" The EMBO Journal (2002) pp. 5711-5720, vol. 21, No. 21.
Akiva, P. et al., "Transcription-Mediated Gene Fusion in the Human Genome" Genome Research (2006) pp. 30-36, vol. 16.
Groskopf, J. et al., "APTIMA PCA3 Molecular Urine Test: Development of a Method to Aid in the Diagnosis of Prostate Cancer" Clinical Chemistry (2006) pp. 1089-1095, vol. 52.
Hessels, D. et al., "Detection of TMPRSS2-ERG Fusion Transcripts and Prostate Cancer Antigen 3 in Urinary Sediments May Improve Diagnosis of Prostate Cancer" Clinical Cancer Research (Sep. 1, 2007) pp. 5103-5108, vol. 13, No. 17.
Tomlins, S.A. et al., "ETS Gene Fusions in Prostate Cancer: From Discovery to Daily Clinical Practice" European Urology (2009) pp. 275-286, vol. 56, No. 2.
AACR Special Conference, Advances in Prostate Cancer Research (Jan. 21-24, 2009) Post Session A, Thursday, Jan. 22, 7:30pm-10:00pm, Table of Contents of poster session. seven pages.
Supplementary Information, Nature doi:10.1038/nature07638, pp. 1-42, Maher et al. 2009.
Pflüger, D., "Towards Understanding of Prostate Cancer Heterogeneity" Faculty of Medicine of Ulm University, Materprogram Molecular Medicine, Master's Thesis (Sep. 10, 2008).
Maher C.A. et al., "Transcriptions Sequencing to Detect Gene Fusions in Cancer", *Nature* 458(7234):1-42 (Mar. 5, 2009), along with Supplementary Information-Supplementary Discussion pp. 1-42.
Rickman D.S. et al., "SLC45A3-ELK4 is a Novel and Frequent Erythroblast Transformation-Specific Fusion Transcript in Prostate Cancer", *Cancer Research* 69(7):2734-2738 (Apr. 1, 2009), along with Supplemental Information pp. 1-8.
Pflueger, D. et al, "SLC45A3 is a Common ETS Family Fusion Partner in Prostate Cancer", presented in Poster Session A of the AACR Special Conference on Jan. 21-24, 2009.

* cited by examiner

PCR:

SLC45A3-ELK4 v1

SLC45A3-ELK4 v2

SLC45A3-ELK4 v3

SLC45A3-ELK4 v4

5' RACE:

SLC45A3-ELK4 v5

SEQUENCE LISTING

<160> NUMBER OF SEQ ID NOS: 38

<210> SEQ ID NO 1
<211> LENGTH: 325
<212> TYPE: DNA
<213> ORGANISM: Homo sapiens

<400> SEQUENCE: 1

```
aacctggaga tttaaaagcc gccggctggc gcgcgtgggg ggcaaggaag ggggggcgga         60
accagcctgc acgcgctggc tccgggtgac agccgcgcgc ctcggccagc tcattgctat        120
ggacagtgct atcaccctgt ggcagttcct tcttcagctc ctgcagaagc ctcagaacaa        180
gcacatgatc tgttggacct ctaatgatgg gcagtttaag cttttgcagg cagaagaggt        240
ggctcgtctc tgggggattc gcaagaacaa gcctaacatg aattatgaca aactcagccg        300
agccctcaga tactattatg taaag                                              325
```

<210> SEQ ID NO 2
<211> LENGTH: 615
<212> TYPE: DNA
<213> ORGANISM: Homo sapiens

<400> SEQUENCE: 2

```
aacctggaga tttaaaagcc gccggctggc gcgcgtgggg ggcaaggaag ggggggcgga         60
accagcctgc acgcgctggc tccgggtgac agccgcgcgc ctcggccagg atctgagtga        120
tgagacgtgt ccccactgag gtgccccaca gcagcaggtg ttgagcatgg gctgagaagc        180
tggaccggca ccaaagggct ggcagaaatg gcgcctggct gattcctag gcagttggcg         240 gcagcaagga ggagaggccg cagcttctgg agcagagccg agacaagca gttctggagt         300 gcctgaacgg cccctgagc cctacccgcc tggcccacta ggtccagag gctgtgggtg          360 agccgcctgc tgcggcaccg gaaagcccag ctcttgctgg tcaacctgct aacctttggc        420
ctggaggtgt gtttggccgc aggcatcacc tatgtgccgc ctctgctgct ggaagtgggg        480
gtagaggaga agttcatgac catggtgctg gctcattgct atggacagtg ctatcaccct        540
gtggcagttc cttcttcagc tcctgcagaa gcctcagaac aagcacatga tctgttggac        600
ctctaatgat gggca                                                         615
```

<210> SEQ ID NO 3
<211> LENGTH: 379
<212> TYPE: DNA
<213> ORGANISM: Homo sapiens

<400> SEQUENCE: 3

```
aacctggaga tttaaaagcc gccggctggc gcgcgtgggg ggcaaggaag ggggggcgga         60
accagcctgc acgcgctggc tccgggtgac agccgcgcgc ctcggccagg atctgagtga        120
tgagacgtgt ccccactgag gtgccccaca gcagctcttg ctggtcaacc tgctaacctt       180
tggcctggag gtgtgtttgg ccgcaggcat cacctatgtg ccgcctctgc tgctggaagt       240
gggggtagag gagaagttca tgaccatggt gctggctcat tgctatggac agtgctatca      300
ccctgtggca gttccttctt cagctcctgc agaagcctca gaacaagcac atgatctgtt      360
ggacctctaa tgatgggca                                                    379
```

<210> SEQ ID NO 4
<211> LENGTH: 371
<212> TYPE: DNA
<213> ORGANISM: Homo sapiens

<400> SEQUENCE: 4

```
aacctggaga tttaaaagcc gccggctggc gcgcgtgggg ggcaaggaag ggggggcgga         60
accagcctgc acgcgctggc tccgggtgac agccgcgcgc ctcggccagg atctgagtga        120
tgagacgtgt ccccactgag gtgcccctac acactggcct ccctctacca ccgggagaag       180
```

```
cagtggagga cttttgaccc gtctcctcac cttctgatac acaccaacca accagtcaac    240
cagccattgc tgtttactgg atacctgctc attgctatgg acagtgctat caccctgtgg    300
cagttccttc ttcagctcct gcagaagcct cagaacaagc acatgatctg ttggacctct    360
aatgatgggc a                                                         371
```

```
<210> SEQ ID NO 5
<211> LENGTH: 774
<212> TYPE: DNA
<213> ORGANISM: Homo sapiens

<400> SEQUENCE: 5
```

```
tgggccccac cgagccagca gaagggctgt cggccccctc cttgtcgccc cactgctgtc     60
catgccgggc ccgcttggct ttccggaacc tgggcgccct gcttccccgg ctgcaccagc    120
tgtgctgccg catgccccgc accctgcgcc ggctcttcgt ggctgagctg tgcagctgga    180
tggcactcat gaccttcacg ctgttttaca cggatttcgt gggcgagggg ctgtaccagg    240
gcgtgcccag agctgagccg ggcaccgagg cccggagaca ctatgatgaa ggcgttcgga    300
tgggcagcct ggggctgttc ctgcagtgcg ccatctccct ggtcttctct ctggtcatgg    360
accggctggt gcagcgattc ggcactcgag cagtctattt ggccagtgtg cagcttttcc    420
ctgtggctgc cggtgccaca tgcctgtccc acagtgtggc cgtggtgaca gcttcagccg    480
ccctcaccgg gttcaccttc tcagccctgc agatcctgcc ctacacactg gcctccctct    540
accaccggga gaagcagtgg aggacttttg acccgtctcc tcaccttctg atacacacca    600
accaaccagt caaccagcca ttgctgttta ctggatacct gctcattgct atggacagtg    660
ctatcaccct gtggcagttc cttcttcagc tcctgcagaa gcctcagaac aagcacatga    720
tctgttggac tctaatgat gggcagttta agcttttgca ggcagaagag gtgg           774
```

```
<210> SEQ ID NO 6
<211> LENGTH: 3398
<212> TYPE: DNA
<213> ORGANISM: Homo sapiens
<220> FEATURE:
<221> NAME/KEY: misc_feature
<222> LOCATION: (1)..(109)
<223> OTHER INFORMATION: Exon 1
<220> FEATURE:
<221> NAME/KEY: misc_feature
<222> LOCATION: (110)..(511)
<223> OTHER INFORMATION: Exon 2
<220> FEATURE:
<221> NAME/KEY: CDS
<222> LOCATION: (340)..(2001)
<220> FEATURE:
<221> NAME/KEY: misc_feature
<222> LOCATION: (512)..(1297)
<223> OTHER INFORMATION: Exon 3
<220> FEATURE:
<221> NAME/KEY: misc_feature
<222> LOCATION: (1298)..(1563)
<223> OTHER INFORMATION: Exon 4
<220> FEATURE:
<221> NAME/KEY: misc_feature
<222> LOCATION: (1564)..(3382)
<223> OTHER INFORMATION: Exon 5

<400> SEQUENCE: 6
```

```
aacctggaga tttaaaagcc gccggctggc gcgcgtgggg ggcaaggaag gggggcgga     60 accagcctgc acgcgctggc tccgggtgac agccgcgcgc ctcggccagg atctgagtga   120
tgagacgtgt ccccactgag gtgccccaca gcagcaggtg ttgagcatgg gctgagaagc   180
```

```
tggaccggca ccaaagggct ggcagaaatg ggcgcctggc tgattcctag gcagttggcg      240
gcagcaagga ggagaggccg cagcttctgg agcagagccg agacgaagca gttctggagt      300
gcctgaacgg cccctgagc cctacccgcc tggcccact atg gtc cag agg ctg         354
                                            Met Val Gln Arg Leu
                                            1               5 tgg gtg agc cgc ctg ctg cgg cac cgg aaa gcc cag ctc ttg ctg gtc       402
Trp Val Ser Arg Leu Leu Arg His Arg Lys Ala Gln Leu Leu Leu Val
            10                  15                  20 aac ctg cta acc ttt ggc ctg gag gtg tgt ttg gcc gca ggc atc acc       450
Asn Leu Leu Thr Phe Gly Leu Glu Val Cys Leu Ala Ala Gly Ile Thr
                25                  30                  35 tat gtg ccg cct ctg ctg ctg gaa gtg ggg gta gag gag aag ttc atg       498
Tyr Val Pro Pro Leu Leu Leu Glu Val Gly Val Glu Glu Lys Phe Met
        40                  45                  50 acc atg gtg ctg ggc att ggt cca gtg ctg ggc ctg gtc tgt gtc ccg       546
Thr Met Val Leu Gly Ile Gly Pro Val Leu Gly Leu Val Cys Val Pro
55                  60                  65 ctc cta ggc tca gcc agt gac cac tgg cgt gga cgc tat ggc cgc cgc       594
Leu Leu Gly Ser Ala Ser Asp His Trp Arg Gly Arg Tyr Gly Arg Arg
70                  75                  80                  85 cgg ccc ttc atc tgg gca ctg tcc ttg ggc atc ctg agc ctc ttt           642
Arg Pro Phe Ile Trp Ala Leu Ser Leu Gly Ile Leu Leu Ser Leu Phe
                90                  95                  100 ctc atc cca agg gcc ggc tgg cta gca ggg ctg ctg tgc ccg gat ccc       690
Leu Ile Pro Arg Ala Gly Trp Leu Ala Gly Leu Leu Cys Pro Asp Pro
                105                 110                 115 agg ccc ctg gag ctg gca ctc atc ctg ggc gtg ggg ctg ctg gac           738
Arg Pro Leu Glu Leu Ala Leu Ile Leu Gly Val Gly Leu Leu Asp
            120                 125                 130 ttc tgt ggc cag gtg tgc ttc act cca ctg gag gcc ctc tct gac           786
Phe Cys Gly Gln Val Cys Phe Thr Pro Leu Glu Ala Leu Leu Ser Asp
135                 140                 145 ctc ttc cgg gac ccg gac cac tgt cgc cag gcc tac tct gtc tat gcc       834
Leu Phe Arg Asp Pro Asp His Cys Arg Gln Ala Tyr Ser Val Tyr Ala
150                 155                 160                 165 ttc atg atc agt ctt ggg ggc tgc ctg ggc tac ctc ctg cct gcc att       882
Phe Met Ile Ser Leu Gly Gly Cys Leu Gly Tyr Leu Leu Pro Ala Ile
                170                 175                 180 gac tgg gac acc agt gcc ctg gcc ccc tac ctg ggc acc cag gag gag       930
Asp Trp Asp Thr Ser Ala Leu Ala Pro Tyr Leu Gly Thr Gln Glu Glu
                185                 190                 195 tgc ctc ttt ggc ctg ctc acc ctc atc ttc ctc acc tgc gta gca gcc       978
Cys Leu Phe Gly Leu Leu Thr Leu Ile Phe Leu Thr Cys Val Ala Ala
            200                 205                 210 aca ctg ctg gtg gct gag gag gca gcg ctg ggc ccc acc gag cca gca      1026
Thr Leu Leu Val Ala Glu Glu Ala Ala Leu Gly Pro Thr Glu Pro Ala
            215                 220                 225 gaa ggg ctg tcg gcc ccc tcc ttg tcg ccc cac tgc tgt cca tgc cgg      1074
Glu Gly Leu Ser Ala Pro Ser Leu Ser Pro His Cys Cys Pro Cys Arg
230                 235                 240                 245 gcc cgc ttg gct ttc cgg aac ctg ggc gcc ctg ctt ccc cgg ctg cac      1122
Ala Arg Leu Ala Phe Arg Asn Leu Gly Ala Leu Leu Pro Arg Leu His
                250                 255                 260 cag ctg tgc tgc cgc atg ccc cgc acc ctg cgc cgg ctc ttc gtg gct      1170
Gln Leu Cys Cys Arg Met Pro Arg Thr Leu Arg Arg Leu Phe Val Ala
            265                 270                 275 gag ctg tgc agc tgg atg gca ctc atg acc ttc acg ctg ttt tac acg      1218
Glu Leu Cys Ser Trp Met Ala Leu Met Thr Phe Thr Leu Phe Tyr Thr
```

-continued

```
                                  280                 285                 290
gat ttc gtg ggc gag ggg ctg tac cag ggc gtg ccc aga gct gag ccg      1266
Asp Phe Val Gly Glu Gly Leu Tyr Gln Gly Val Pro Arg Ala Glu Pro
    295                 300                 305 ggc acc gag gcc cgg aga cac tat gat gaa ggc gtt cgg atg ggc agc      1314
Gly Thr Glu Ala Arg Arg His Tyr Asp Glu Gly Val Arg Met Gly Ser
310                 315                 320                 325 ctg ggg ctg ttc ctg cag tgc gcc atc tcc ctg gtc ttc tct ctg gtc      1362
Leu Gly Leu Phe Leu Gln Cys Ala Ile Ser Leu Val Phe Ser Leu Val
                330                 335                 340 atg gac cgg ctg gtg cag cga ttc ggc act cga gca gtc tat ttg gcc      1410
Met Asp Arg Leu Val Gln Arg Phe Gly Thr Arg Ala Val Tyr Leu Ala
            345                 350                 355 agt gtg gca gct ttc cct gtg gct gcc ggt gcc aca tgc ctg tcc cac      1458
Ser Val Ala Ala Phe Pro Val Ala Ala Gly Ala Thr Cys Leu Ser His
        360                 365                 370 agt gtg gcc gtg gtg aca gct tca gcc gcc ctc acc ggg ttc acc ttc      1506
Ser Val Ala Val Val Thr Ala Ser Ala Ala Leu Thr Gly Phe Thr Phe
    375                 380                 385 tca gcc ctg cag atc ctg ccc tac aca ctg gcc tcc ctc tac cac cgg      1554
Ser Ala Leu Gln Ile Leu Pro Tyr Thr Leu Ala Ser Leu Tyr His Arg
390                 395                 400                 405 gag aag cag gtg ttc ctg ccc aaa tac cga ggg gac act gga ggt gct      1602
Glu Lys Gln Val Phe Leu Pro Lys Tyr Arg Gly Asp Thr Gly Gly Ala
                410                 415                 420 agc agt gag gac agc ctg atg acc agc ttc ctg cca ggc cct aag cct      1650
Ser Ser Glu Asp Ser Leu Met Thr Ser Phe Leu Pro Gly Pro Lys Pro
            425                 430                 435 gga gct ccc ttc cct aat gga cac gtg ggt gct gga ggc agt ggc ctg      1698
Gly Ala Pro Phe Pro Asn Gly His Val Gly Ala Gly Gly Ser Gly Leu
        440                 445                 450 ctc cca cct cca ccc gcg ctc tgc ggg gcc tct gcc tgt gat gtc tcc      1746
Leu Pro Pro Pro Pro Ala Leu Cys Gly Ala Ser Ala Cys Asp Val Ser
    455                 460                 465 gta cgt gtg gtg gtg ggt gag ccc acc gag gcc agg gtg gtt ccg ggc      1794
Val Arg Val Val Val Gly Glu Pro Thr Glu Ala Arg Val Val Pro Gly
470                 475                 480                 485 cgg ggc atc tgc ctg gac ctc gcc atc ctg gat agt gcc ttc ctg ctg      1842
Arg Gly Ile Cys Leu Asp Leu Ala Ile Leu Asp Ser Ala Phe Leu Leu
                490                 495                 500 tcc cag gtg gcc cca tcc ctg ttt atg ggc tcc att gtc cag ctc agc      1890
Ser Gln Val Ala Pro Ser Leu Phe Met Gly Ser Ile Val Gln Leu Ser
            505                 510                 515 cag tct gtc act gcc tat atg gtg tct gcc gca ggc ctg ggt ctg gtc      1938
Gln Ser Val Thr Ala Tyr Met Val Ser Ala Ala Gly Leu Gly Leu Val
        520                 525                 530 gcc att tac ttt gct aca cag gta gta ttt gac aag agc gac ttg gcc      1986
Ala Ile Tyr Phe Ala Thr Gln Val Val Phe Asp Lys Ser Asp Leu Ala
    535                 540                 545 aaa tac tca gcg tag aaaacttcca gcacattggg gtggagggcc tgcctcactg      2041
Lys Tyr Ser Ala
550 ggtcccagct ccccgctcct gttagcccca tggggctgcc gggctggccg ccagtttctg    2101 ttgctgccaa agtaatgtgg ctctctgctg ccaccctgtg ctgctgaggt gcgtagctgc    2161 acagctgggg gctggggcgt ccctctcctc tctccccagt tctagggct gcctgactgg     2221 aggccttcca aggggggttc agtctggact tatacaggga ggccagaagg gctccatgca    2281 ctggaatgcg gggactctgc aggtggatta cccaggctca gggttaacag ctagcctcct    2341
```

```
agttgagaca cacctagaga agggttttg ggagctgaat aaactcagtc acctggtttc    2401
ccatctctaa gcccttaac ctgcagcttc gtttaatgta gctcttgcat gggagtttct    2461
aggatgaaac actcctccat gggatttgaa catatgaaag ttatttgtag gggaagagtc    2521
ctgaggggca acacacaaga accaggtccc ctcagcccac agcactgtct ttttgctgat    2581 ccaccccct cttaccttt atcaggatgt ggcctgttgg tccttctgtt gccatcacag      2641
agacacaggc atttaaatat ttaacttatt tatttaacaa agtagaaggg aatccattgc    2701
tagcttttct gtgttggtgt ctaatatttg ggtagggtgg gggatcccca acaatcaggt    2761
cccctgagat agctggtcat tgggctgatc attgccagaa tcttcttctc ctggggtctg    2821 gcccccaaa atgcctaacc caggaccttg gaaattctac tcatcccaaa tgataattcc     2881
aaatgctgtt acccaaggtt agggtgttga aggaaggtag agggtggggc ttcaggtctc    2941
aacggcttcc ctaaccaccc ctcttctctt ggcccagcct ggttcccccc acttccactc    3001
ccctctactc tctctaggac tgggctgatg aaggcactgc ccaaaatttc ccctaccccc    3061
aactttcccc tacccccaac tttccccacc agctccacaa ccctgtttgg agctactgca    3121
ggaccagaag cacaaagtgc ggtttcccaa gcctttgtcc atctcagccc ccagagtata    3181
tctgtgcttg gggaatctca cacagaaact caggagcacc ccctgcctga gctaagggag    3241
gtcttatctc tcaggggggg tttaagtgcc gtttgcaata atgtcgtctt atttatttag    3301
cggggtgaat attttatact gtaagtgagc aatcagagta taatgtttat ggtgacaaaa    3361
ttaaaggctt tcttatatgt taaaaaaaaa aaaaaaa                             3398

<210> SEQ ID NO 7
<211> LENGTH: 3034
<212> TYPE: DNA
<213> ORGANISM: Homo sapiens
<220> FEATURE:
<221> NAME/KEY: misc_feature
<222> LOCATION: (1)..(1241)
<223> OTHER INFORMATION: Exon 1
<220> FEATURE:
<221> NAME/KEY: misc_feature
<222> LOCATION: (1242)..(1457)
<223> OTHER INFORMATION: Exon 2
<220> FEATURE:
<221> NAME/KEY: CDS
<222> LOCATION: (1251)..(2546)
<220> FEATURE:
<221> NAME/KEY: misc_feature
<222> LOCATION: (1458)..(2330)
<223> OTHER INFORMATION: Exon 3a
<220> FEATURE:
<221> NAME/KEY: misc_feature
<222> LOCATION: (2331)..(2447)
<223> OTHER INFORMATION: Exon 4
<220> FEATURE:
<221> NAME/KEY: misc_feature
<222> LOCATION: (2448)..(2985)
<223> OTHER INFORMATION: Exon 5
<220> FEATURE:
<221> NAME/KEY: misc_feature
<222> LOCATION: (2985)..(2985)
<223> OTHER INFORMATION: POly A site

<400> SEQUENCE: 7
tttcttgtta aacaaacacc taatttattt cttggaggtt ttgttcagct gtcctaattt    60
atgactttac attccttctg gtgctaaact gctcaagtag cctcttgtat caagtgtgac    120
ctgattcctg aagaatttta cttaatgaga acctctaagc tagaaactct tgctaggtgt    180
ttcatgcacc ttatttctt taatcattac aacaactcta agattgggtt ctctccacct    240
```

```
tataaatgat gactgtttta gagaggttaa ggttgcttaa aattggtgag ttagtgaggg      300
gtagagccac gaatggattt ctggtcgctg cctccatcgt cagggcaagc ttttcccacg      360
actccagcgc ttccatttgt cagtccccag gctagaaagc cacagtgcta atttagtatt      420
tatcaagcgt ttgtagtgtc ctgggatctg gcacttcgat gagaaagctg tgacggcccc      480
aacttctaac agcgagtggt aaggaggacg agggacacag gagggaggag actctcccca      540
aagcttagca ccaacagaag tggtcccccg caggttgctc tgcgagcgcc acctcttccc      600
tccaaccgag gagaaagtgg cgcgcctttg aggagtccga ggtcccggcc caggcggcag      660
cttgggtcct gcgggttcc ggacgggcgc ctcaggacc tggaagcaac cgcaccgaac        720
gcgacggaga gcggcgagac gactccagga ggcgcccgag ctacatcccc cggccacacc      780
aaacccgggt ttgctggcag acgcggctca cgacacccct tagggtcgca gcccctcccc      840
cggaagtgac gtgtagcgac tacggcgtct gggagggacc caggagcagt cgggggggttt     900 gagagtggcg gcgccgcgg agggcctggc aggccccgcc gctgcaagga acgcccccgaa      960 cgcgcgcgcc cggcgtgtag cggccccaag accccgcgccg ccgctgccgc gtgcgggggc     1020
ggggagggcg gggcgccagg agccgcgcg cggagatg cgggcggctg cgggcacccg         1080
gcgggctcgg cttggccgcc gccgccttct acggctccgc cgcggggtc gcagcggctg       1140 ccgcgccgtc ctcgagtttc cagcgtgagg aggaggctga gggcggagag gcgcatcgtg      1200
ttcgaggcgg agaccgaggg ggagccccgc gcgcggcgtc gctcattgct atg gac         1256
                                                          Met Asp
                                                           1 agt gct atc acc ctg tgg cag ttc ctt ctt cag ctc ctg cag aag cct        1304
Ser Ala Ile Thr Leu Trp Gln Phe Leu Leu Gln Leu Leu Gln Lys Pro
         5                  10                  15 cag aac aag cac atg atc tgt tgg acc tct aat gat ggg cag ttt aag        1352
Gln Asn Lys His Met Ile Cys Trp Thr Ser Asn Asp Gly Gln Phe Lys
     20                  25                  30 ctt ttg cag gca gaa gag gtg gct cgt ctc tgg ggg att cgc aag aac        1400
Leu Leu Gln Ala Glu Glu Val Ala Arg Leu Trp Gly Ile Arg Lys Asn
 35                  40                  45                  50 aag cct aac atg aat tat gac aaa ctc agc cga gcc ctc aga tac tat        1448
Lys Pro Asn Met Asn Tyr Asp Lys Leu Ser Arg Ala Leu Arg Tyr Tyr
                 55                  60                  65 tat gta aag aat atc atc aaa aaa gtg aat ggt cag aag ttt gtg tac        1496
Tyr Val Lys Asn Ile Ile Lys Lys Val Asn Gly Gln Lys Phe Val Tyr
             70                  75                  80 aag ttt gtc tct tat cca gag att ttg aac atg gat cca atg aca gtg        1544
Lys Phe Val Ser Tyr Pro Glu Ile Leu Asn Met Asp Pro Met Thr Val
         85                  90                  95 ggc agg att gag ggt gac tgt gaa agt tta aac ttc agt gaa gtc agc        1592
Gly Arg Ile Glu Gly Asp Cys Glu Ser Leu Asn Phe Ser Glu Val Ser
     100                 105                 110 agc agt tcc aaa gat gtg gag aat gga ggg aaa gat aaa cca cct cag        1640
Ser Ser Ser Lys Asp Val Glu Asn Gly Gly Lys Asp Lys Pro Pro Gln
115                 120                 125                 130 cct ggt gcc aag acc tct agc cgc aat gac tac ata cac tct ggc tta        1688
Pro Gly Ala Lys Thr Ser Ser Arg Asn Asp Tyr Ile His Ser Gly Leu
                 135                 140                 145 tat tct tca ttt act ctc aac tct ttg aac tcc tcc aat gta aag ctt        1736
Tyr Ser Ser Phe Thr Leu Asn Ser Leu Asn Ser Ser Asn Val Lys Leu
             150                 155                 160 ttc aaa ttg ata aag act gag aat cca gcc gag aaa ctg gca gag aaa        1784
Phe Lys Leu Ile Lys Thr Glu Asn Pro Ala Glu Lys Leu Ala Glu Lys
```

```
                165                 170                 175
aaa tct cct cag gag ccc aca cca tct gtc atc aaa ttt gtc acg aca    1832
Lys Ser Pro Gln Glu Pro Thr Pro Ser Val Ile Lys Phe Val Thr Thr
    180                 185                 190 cct tcc aaa aag cca ccg gtt gaa cct gtt gct gcc acc att tca att    1880
Pro Ser Lys Lys Pro Pro Val Glu Pro Val Ala Ala Thr Ile Ser Ile
195                 200                 205                 210 ggc cca agt att tct cca tct tca gaa gaa act atc caa gct ttg gag    1928
Gly Pro Ser Ile Ser Pro Ser Ser Glu Glu Thr Ile Gln Ala Leu Glu
                215                 220                 225 aca ttg gtt tcc cca aaa ctg cct tcc ctg gaa gcc cca acc tct gcc    1976
Thr Leu Val Ser Pro Lys Leu Pro Ser Leu Glu Ala Pro Thr Ser Ala
        230                 235                 240 tct aac gta atg act gct ttt gcc acc aca cca ccc att tcg tcc ata    2024
Ser Asn Val Met Thr Ala Phe Ala Thr Thr Pro Pro Ile Ser Ser Ile
    245                 250                 255 ccc cct ttg cag gaa cct ccc aga aca cct tca cca cca ctg agt tct    2072
Pro Pro Leu Gln Glu Pro Pro Arg Thr Pro Ser Pro Pro Leu Ser Ser
260                 265                 270 cac cca gac atc gac aca gac att gat tca gtg gct tct cag cca atg    2120
His Pro Asp Ile Asp Thr Asp Ile Asp Ser Val Ala Ser Gln Pro Met
275                 280                 285                 290 gaa ctt cca gag aat ttg tca ctg gag cct aaa gac cag gat tca gtc    2168
Glu Leu Pro Glu Asn Leu Ser Leu Glu Pro Lys Asp Gln Asp Ser Val
                295                 300                 305 ttg cta gaa aag gac aaa gta aat aat tca tca aga tcc aag aaa ccc    2216
Leu Leu Glu Lys Asp Lys Val Asn Asn Ser Ser Arg Ser Lys Lys Pro
        310                 315                 320 aaa ggg tta gaa ctg gca ccc acc ctt gtg atc acg agc agt gat cca    2264
Lys Gly Leu Glu Leu Ala Pro Thr Leu Val Ile Thr Ser Ser Asp Pro
    325                 330                 335 agc cca ctg gga ata ctg agc cca tct ctc cct aca gct tct ctt aca    2312
Ser Pro Leu Gly Ile Leu Ser Pro Ser Leu Pro Thr Ala Ser Leu Thr
340                 345                 350 cca gca ttt ttt tca cag aca ccc atc ata ctg act cca agc ccc ttg    2360
Pro Ala Phe Phe Ser Gln Thr Pro Ile Ile Leu Thr Pro Ser Pro Leu
355                 360                 365                 370 ctc tcc agt atc cac ttc tgg agt act ctc agt cct gtt gct ccc cta    2408
Leu Ser Ser Ile His Phe Trp Ser Thr Leu Ser Pro Val Ala Pro Leu
                375                 380                 385 agt cca gcc aga ctg caa ggt gct aac aca ctt ttc cag ttt cct tct    2456
Ser Pro Ala Arg Leu Gln Gly Ala Asn Thr Leu Phe Gln Phe Pro Ser
        390                 395                 400 gta ctg aac agt cat ggg cca ttc act ctg tct ggg ctg gat gga cct    2504
Val Leu Asn Ser His Gly Pro Phe Thr Leu Ser Gly Leu Asp Gly Pro
    405                 410                 415 tcc acc cct ggc cca ttt tcc cca gac cta cag aag aca taa             2546
Ser Thr Pro Gly Pro Phe Ser Pro Asp Leu Gln Lys Thr
420                 425                 430 cctatgcact tgtggaatga gagaaccgag gaacgaagaa acagacattc aacatgattg    2606
catttgaagt gagcaattga tagttctaca atgctgataa tagactattg tgattttgc     2666 cattccccat tgaaacatc ttttaggat tctctttgaa taggactcaa gttggactat       2726
atgtataaaa atgccttaat tggagtctaa actccacctc cctctgtctt ttccttttct    2786
ttttctttcc ttccttcctt ttcttttctc ctttaaaaat attttgagct tgtgctgaa     2846 gaagtttttg gtgggctta gtgactgtgc tttgcaaaag caattaagaa caaagttact    2906
ccttctggct attgggaccc tttggccagg aaaaattatg cttagaatct attatttaaa    2966
```

```
gaaatatttg tgaaatgaaa aaaaaaaaaa aaaaaaaaaa aaaaaaaaaa aaaaaaaaaa    3026
aaaaaaaa                                                              3034

<210> SEQ ID NO 8
<211> LENGTH: 3077
<212> TYPE: DNA
<213> ORGANISM: Homo sapiens
<220> FEATURE:
<221> NAME/KEY: misc_feature
<222> LOCATION: (1)..(1241)
<223> OTHER INFORMATION: Exon 1
<220> FEATURE:
<221> NAME/KEY: misc_feature
<222> LOCATION: (1242)..(1457)
<223> OTHER INFORMATION: Exon 2
<220> FEATURE:
<221> NAME/KEY: CDS
<222> LOCATION: (1251)..(2468)
<220> FEATURE:
<221> NAME/KEY: misc_feature
<222> LOCATION: (1458)..(3028)
<223> OTHER INFORMATION: Exon 3b
<220> FEATURE:
<221> NAME/KEY: misc_feature
<222> LOCATION: (3006)..(3011)
<223> OTHER INFORMATION: Poly A signal
<220> FEATURE:
<221> NAME/KEY: misc_feature
<222> LOCATION: (3028)..(3028)
<223> OTHER INFORMATION: Poly A site

<400> SEQUENCE: 8
tttcttgtta aacaaacacc taatttattt cttggaggtt ttgttcagct gtcctaattt     60
atgactttac attccttctg gtgctaaact gctcaagtag cctcttgtat caagtgtgac    120
ctgattcctt aagaatttta cttaatgaga acctctaagc tagaaactct tgctaggtgt    180
ttcatgcacc ttattttctt taatcattac aacaactcta agattgggtt ctctccacct    240
tataaatgat gactgtttta gagaggttaa ggttgcttaa aattggtgag ttagtgaggg    300
gtagagccac gaatggattt ctggtcgctg cctccatcgt cagggcaagc ttttcccacg    360
actccagcgc ttccatttgt cagtcccccag gctagaaagc cacagtgcta atttagtatt    420
tatcaagcgt ttgtagtgtc ctgggatctg gcacttcgat gagaaagctg tgacggcccc    480
aacttctaac agcgagtggt aaggaggacg agggacacag gagggaggag actctcccca    540
aagcttagca ccaacagaag tggtcccccg caggttgctc tgcgagcgcc acctcttccc    600
tccaaccgag gagaaagtgg cgcgcctttg aggagtccga ggtcccggcc caggcggcag    660
cttgggtcct ggcgggttcc ggacgggcgc ctcagggacc tggaagcaac cgcaccgaac    720
gcgacggaga gcggcgagac gactccagga ggcgcccgag ctacatcccc cggccacacc    780
aaacccgggt ttgctggcag acgcggctca cgacacccct tagggtcgca gcccctcccc    840
cggaagtgac gtgtagcgac tacgcgtct gggagggacc caggagcagt cgggggggttt    900 gagagtggcg gcgccgcgg agggcctggc aggccccgcc gctgcaagga acgccccgaa    960
cgcgcgcgcc cggcgtgtag cggccccaag accgcgccg ccgctgccgc gtgcgggggc    1020
ggggagggcg gggcgccagg agccgcgcg cggagatg cggcggctg cgggcacccg    1080 gcgggctcgg cttggccgcc gccgccttct acggctccgc cgcggggtc gcagcggctg    1140 ccgcgccgtc ctcgagtttc cagcgtgagg aggaggctga gggcggagag gcgcatcgtg    1200
ttcgaggcgg agaccgaggg ggagccccgc gcgcggcgtc gctcattgct atg gac    1256
                                                           Met Asp
                                                             1
```

```
agt gct atc acc ctg tgg cag ttc ctt ctt cag ctc ctg cag aag cct     1304
Ser Ala Ile Thr Leu Trp Gln Phe Leu Leu Gln Leu Leu Gln Lys Pro
        5                  10                  15 cag aac aag cac atg atc tgt tgg acc tct aat gat ggg cag ttt aag     1352
Gln Asn Lys His Met Ile Cys Trp Thr Ser Asn Asp Gly Gln Phe Lys
 20                  25                  30 ctt ttg cag gca gaa gag gtg gct cgt ctc tgg ggg att cgc aag aac     1400
Leu Leu Gln Ala Glu Glu Val Ala Arg Leu Trp Gly Ile Arg Lys Asn
35                  40                  45                  50 aag cct aac atg aat tat gac aaa ctc agc cga gcc ctc aga tac tat     1448
Lys Pro Asn Met Asn Tyr Asp Lys Leu Ser Arg Ala Leu Arg Tyr Tyr
                55                  60                  65 tat gta aag aat atc atc aaa aaa gtg aat ggt cag aag ttt gtg tac     1496
Tyr Val Lys Asn Ile Ile Lys Lys Val Asn Gly Gln Lys Phe Val Tyr
         70                  75                  80 aag ttt gtc tct tat cca gag att ttg aac atg gat cca atg aca gtg     1544
Lys Phe Val Ser Tyr Pro Glu Ile Leu Asn Met Asp Pro Met Thr Val
             85                  90                  95 ggc agg att gag ggt gac tgt gaa agt tta aac ttc agt gaa gtc agc     1592
Gly Arg Ile Glu Gly Asp Cys Glu Ser Leu Asn Phe Ser Glu Val Ser
        100                 105                 110 agc agt tcc aaa gat gtg gag aat gga ggg aaa gat aaa cca cct cag     1640
Ser Ser Ser Lys Asp Val Glu Asn Gly Gly Lys Asp Lys Pro Pro Gln
115                 120                 125                 130 cct ggt gcc aag acc tct agc cgc aat gac tac ata cac tct ggc tta     1688
Pro Gly Ala Lys Thr Ser Ser Arg Asn Asp Tyr Ile His Ser Gly Leu
                135                 140                 145 tat tct tca ttt act ctc aac tct ttg aac tcc tcc aat gta aag ctt     1736
Tyr Ser Ser Phe Thr Leu Asn Ser Leu Asn Ser Ser Asn Val Lys Leu
         150                 155                 160 ttc aaa ttg ata aag act gag aat cca gcc gag aaa ctg gca gag aaa     1784
Phe Lys Leu Ile Lys Thr Glu Asn Pro Ala Glu Lys Leu Ala Glu Lys
             165                 170                 175 aaa tct cct cag gag ccc aca cca tct gtc atc aaa ttt gtc acg aca     1832
Lys Ser Pro Gln Glu Pro Thr Pro Ser Val Ile Lys Phe Val Thr Thr
180                 185                 190 cct tcc aaa aag cca ccg gtt gaa cct gtt gct gcc acc att tca att     1880
Pro Ser Lys Lys Pro Pro Val Glu Pro Val Ala Ala Thr Ile Ser Ile
195                 200                 205                 210 ggc cca agt att tct cca tct tca gaa gaa act atc caa gct ttg gag     1928
Gly Pro Ser Ile Ser Pro Ser Ser Glu Glu Thr Ile Gln Ala Leu Glu
                215                 220                 225 aca ttg gtt tcc cca aaa ctg cct tcc ctg gaa gcc cca acc tct gcc     1976
Thr Leu Val Ser Pro Lys Leu Pro Ser Leu Glu Ala Pro Thr Ser Ala
         230                 235                 240 tct aac gta atg act gct ttt gcc acc aca cca ccc att tcg tcc ata     2024
Ser Asn Val Met Thr Ala Phe Ala Thr Thr Pro Pro Ile Ser Ser Ile
             245                 250                 255 ccc cct ttg cag gaa cct ccc aga aca cct tca cca ctg agt tct         2072
Pro Pro Leu Gln Glu Pro Pro Arg Thr Pro Ser Pro Leu Ser Ser
260                 265                 270 cac cca gac atc gac aca gac att gat tca gtg gct tct cag cca atg     2120
His Pro Asp Ile Asp Thr Asp Ile Asp Ser Val Ala Ser Gln Pro Met
275                 280                 285                 290 gaa ctt cca gag aat ttg tca ctg gag cct aaa gac cag gat tca gtc     2168
Glu Leu Pro Glu Asn Leu Ser Leu Glu Pro Lys Asp Gln Asp Ser Val
                295                 300                 305 ttg cta gaa aag gac aaa gta aat aat tca tca aga tcc aag aaa ccc     2216
Leu Leu Glu Lys Asp Lys Val Asn Asn Ser Ser Arg Ser Lys Lys Pro
```

```
                    310                 315                 320
aaa ggg tta gaa ctg gca ccc acc ctt gtg atc acg agc agt gat cca      2264
Lys Gly Leu Glu Leu Ala Pro Thr Leu Val Ile Thr Ser Ser Asp Pro
        325                 330                 335 agc cca ctg gga ata ctg agc cca tct ctc cct aca gct tct ctt aca      2312
Ser Pro Leu Gly Ile Leu Ser Pro Ser Leu Pro Thr Ala Ser Leu Thr
340                 345                 350 cca gca ttt ttt tca cag gta gct tgc tcg ctc ttt atg gtg tca cca      2360
Pro Ala Phe Phe Ser Gln Val Ala Cys Ser Leu Phe Met Val Ser Pro
355                 360                 365                 370 ttg ctt tca ttt att tgc cct ttt aag caa atc cag aat tta tac act      2408
Leu Leu Ser Phe Ile Cys Pro Phe Lys Gln Ile Gln Asn Leu Tyr Thr
                375                 380                 385 caa gtt tgc ttt ctg tta ctt agg ttt gtc tta gaa agg tta tgt gtg      2456
Gln Val Cys Phe Leu Leu Leu Arg Phe Val Leu Glu Arg Leu Cys Val
            390                 395                 400 act gtc atg tga aagttacccc atttctcatc ttaattagga ttgctaaaat          2508
Thr Val Met
        405 agaaagtttg gagtattttc ttaaaaaatt cattgttcta caagtaaata aatattttga    2568 tttttctatt tcctcctaaa gaaagtacac acactctctc gctctctctc ggtcttataa    2628 aactcgttgg tgtcttataa aacaaacagt gataatctca agttagaaaa cagtaggtcc    2688 tgagaaccat aagaaaaatg actggtgtga tgttgagtaa caagttggta cagttacttt    2748 agctatttat taacttgctc atctcataga acattttagt agattttttca cacacctcat   2808 tattaaaaaa aaacaaacat gctggtgtct tggttaccca ttattcctct gtacctgaat    2868 tcaggttggt ttttctattt ggaaaagact ttataaatgt tggcttaaaa agaggttgag    2928 caccagaatc tcagaattta ccaccaaaga actcatccat gtaaccaaaa accacttgta    2988 cccccaaaaa ctattgaaat aaaaatttaa aaatttttaa aaaaaaaaa aaaaaaaaa      3048 aaaaaaaaaa aaaaaaaaaa aaaaaaaaa                                     3077

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
gtccacgact tccagcattt                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
tcaaactcca cccttttccag                                                20

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 11
```
caacaagaca ttttcagtta agggt                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 12
ggcaaaacaa acaggtatgc tataa                                              25

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
acagctttcc ttgctctcca                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
tggcatctga agaggttgaa                                                    20

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 15
attccatcct cagctaacag gtaa                                               24

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 16
caaggtgaca gtgttttgat gg                                                 22

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 17
cataccctta gaggtaggta acagc                                              25

<210> SEQ ID NO 18
<211> LENGTH: 20
<212> TYPE: DNA

```
<213> ORGANISM: Artificial Sequence
<220> FEATURE:
<223> OTHER INFORMATION: Synthetic oligonucleotide primer

<400> SEQUENCE: 18
aagatgtgaa tggcagtgga                                                 20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
cacactgaaa caaaagccac a                                               21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 20
cttttgggca agtggacaac                                                 20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 21
gccagataac ccaggctgta                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 22
gccttcatgc attagccatt                                                 20

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 23
gtgctgttag aaataacttt cctgg                                           25

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 24
tccacactct tcacccatca                                                 20
```

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 25
tccacactct tcacccatca				20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 26
cctgtatgct gagcctcatg				20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 27
tattgggtgc cagaaagtcc				20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 28
ctccctgcag agccagttac				20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 29
ccaacatggg caacatctct				20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 30
tgggttcagg tgatgtcaga				20

<210> SEQ ID NO 31
<211> LENGTH: 20
<212> TYPE: DNA
<213> ORGANISM: Artificial Sequence
<220> FEATURE:

<223> OTHER INFORMATION: Synthetic oligonucleotide primer

<400> SEQUENCE: 31
caagcccttg cacaggttat                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 32
catgggaata gggaatgcac                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 33
aaaccgcact ttgtgcttct                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
cttcaggtct caacggcttc                                              20

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 35
tctctgctcc ctcactctca a                                            21

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 36
tgtgcctctt ccatcgttct                                              20

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 37
ccgcggagta acctggagat tt                                           22

```
<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 38
tgcccatcat tagaggtcca acag                                          24
```

COMPOSITIONS AND METHODS FOR DIAGNOSING PROSTATE CANCER BASED ON DETECTION OF SLC45A3-ELK4 FUSION TRANSCRIPT

CROSS-REFERENCE TO RELATED APPLICATION

This application claims the benefit under 35 U.S.C. §119 (e) of U.S. Provisional Application No. 61/153,835, filed on Feb. 19, 2009.

GOVERNMENT FUNDING

This invention was made with Government support under Grant Number R01 CA125612-01 awarded by National Institutes of Health (NIH)/National Cancer Institute. The United States Government has certain rights in the invention.

FIELD OF THE INVENTION

This invention relates to cancer diagnosis and treatment. More specifically, the invention relates to compositions and methods for diagnosing prostate cancer based on detection of SLC45A3-ELK4 fusion transcript.

BACKGROUND OF THE INVENTION

Chromosome rearrangement of erythroblast transformation specific (ETS) family members in prostate cancer, similar to other translocation tumors, may represent a distinct subclass of prostate cancer, based on studies demonstrating varying morphologic features (Mosquera et al., *J Pathol* 2007; 212: 91-101), survival (Attard et al., *Oncogene* 2008; 27: 253-63; Cheville et al., *J Clin Oncol* 2008; 26: 3930-6; Demichelis et al., *Oncogene* 2007; 26: 4596-9), and a specific expression profile (Setlur et al., *J Natl Cancer Inst* 2008; 100: 815-25). Androgen-regulated genes account for the majority of the 5' genomic regulatory promoter elements fused with ETS genes in prostate cancer (Tomlins et al., *Nature* 2007; 448: 595-9). For example, the promoter of the androgen-regulated transmembrane protease, serine 2 (TMPRSS2) gene is fused to the coding region of members of the ETS family of transcription factors, most commonly v-ets erythroblastosis virus E26 oncogene homolog (avian) (ERG) (Helgeson et al., *Cancer Res* 2008; 68: 73-80; Tomlins et al., *Cancer Res* 2006; 66: 3396-400; Han et al. *Cancer Res* 2008; 68: 7629-37). The presence of these fusion genes can serve as diagnostic markers and rational therapeutic targets for the treatment of prostate cancer and other cancer types. SLC45A3 (solute carrier family 45, member 3), also referred to as prostein, is a prostate-specific, androgen-regulated gene that has been shown to be a 5' partner with ETV1 and ETV5 (Tomlins et al., *Nature* 2007; 448: 595-9; Helgeson et al., *Cancer Res* 2008; 68: 73-80). The majority of the cases demonstrating SLC45A3 rearrangement were seen in conjunction with either ERG (80%) or ETV1 (10%), but the 3' partners for the remaining 10% of SLC45A3 in prostate cancers have not been identified. ELK4 (ETS-domain protein (SRF accessory protein 1)), a member of the ETS family of transcription factors, was recently described as a novel androgen receptor target in LNCaP cells promoting cell growth (Makkonen et al., *Oncogene* 2008; August 21; 27(36):4865-76. Epub 2008 May 12).

SUMMARY OF THE INVENTION

In accordance with the present invention, fusion transcripts between SLC45A3 and ELK4 have been identified for the first time. These transcripts have been shown to be expressed at elevated levels in patients having prostate cancer.

In one embodiment, the invention provides a method of diagnosing cancer, e.g., prostate cancer, in a patient based on detecting elevated levels of a SLC45A3-ELK4 fusion molecule(s) in a patient sample.

In a specific embodiment, the fusion molecule is a transcript representing a fusion between a 5' portion of a SLC45A3 mRNA and a 3' portion of an ELK4 mRNA. In certain embodiments, the fusion transcript contains a 5' portion of a SLC45A3 mRNA which includes at least exon 1 of SLC45A3, fused to a 3' portion of an ELK4 mRNA which includes at least exon 2 of ELK4. In other embodiments, the fusion transcript includes exon 1, and a portion of one or more of exons 2, 3 and 4 of SLC45A3, as well as exon 2 and one or more of downstream exons of ELK4.

Suitable sample sources for use in the detection are biological specimens that contain nucleic acids, examples of which include prostate tissue, blood, urine, semen, prostatic secretions and prostate cells.

Detection of a fusion nucleic acid molecule can be achieved by using a variety of techniques, including hybridization or amplification based techniques. Primers and probes designed to selectively identify the fusion molecules can be used, including those specific for the junction of fusion.

Detection of fusion proteins produced from fusion nucleic acid molecules can be detected by using any of known assays suitable for protein detections, including immuneassays using antibodies specific for fusion proteins, such as antibodies specific for the junction of fusion.

In another embodiment, the invention provides compositions and kits containing reagents useful for use in the diagnostic method of the invention.

In still another embodiment, the invention provides a method of identifying an agent useful for treating cancer such as prostate cancer based on identifying an agent that inhibits a biological function or reduces the level of a SLC45A3-ELK4 fusion molecule in a cell in vitro.

In yet another embodiment, the invention provides a method for treating cancer, e.g., prostate cancer, in a patient, by administering to the patient an agent that inhibits a biological function or reduces the level of a SLC45A3-ELK4 fusion molecule.

Figure 1A:
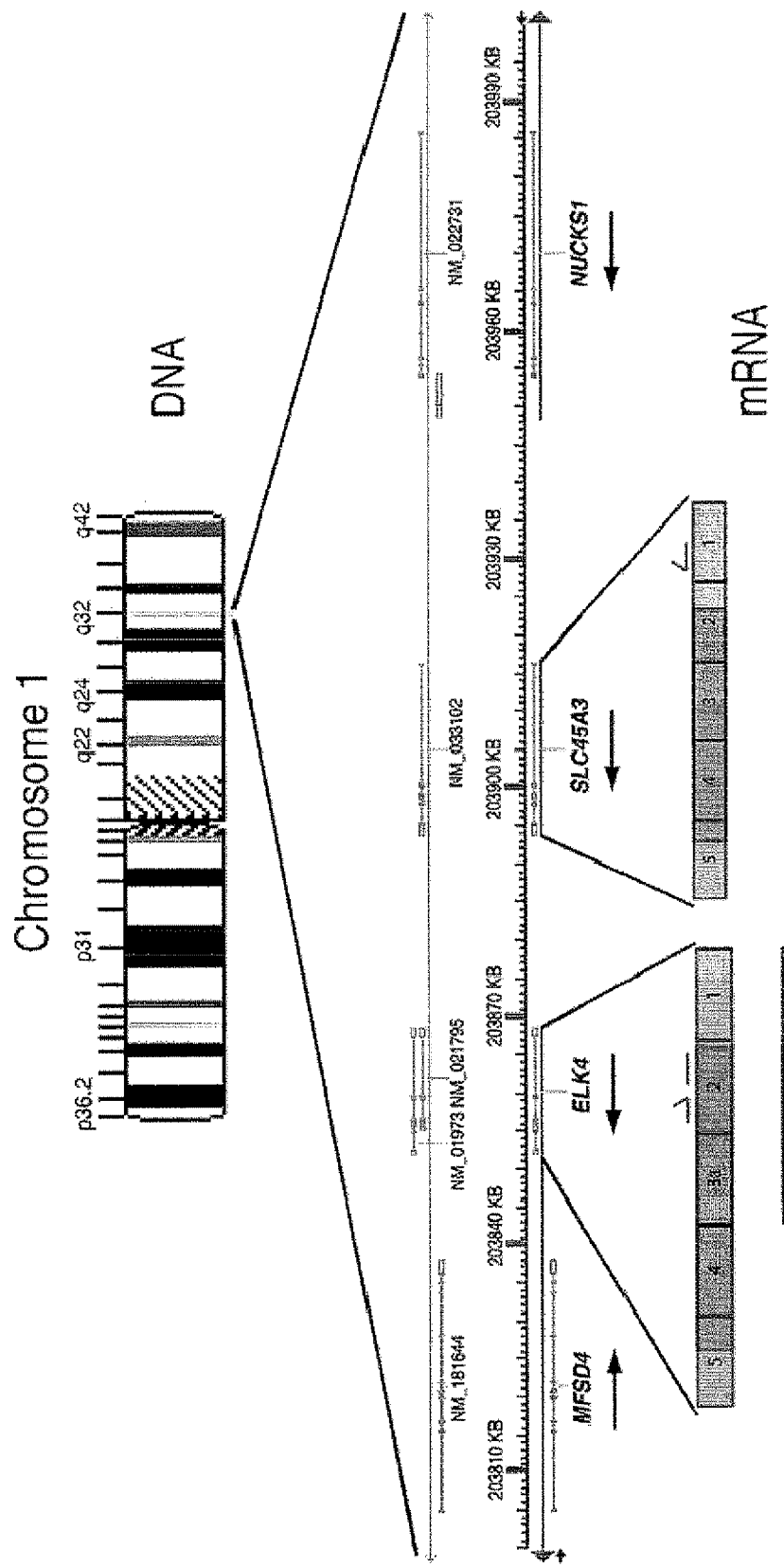
FIGS. 1*a*-1*d*. Detection of SLC45A3-ELK4 mRNA in prostate cancer, benign prostate tissue and LNCaP cells. 1*a*. Schematic of chromosome 1q32.1 (Chr.1q32.1) demonstrating the orientation and relative distance of SLC45A3 and ELK4. Red arrows and bar indicate the SLC45A3-ELK4 TAQMAN assay primers and probe, respectively. 1*b*. TAQMAN expression data of SLC45A3-ELK4 and ELK4 mRNA levels in 31 prostate cancer samples relative to levels measured for an internal control gene (TCFL1) and calibrated to the median of the values obtained from the 6 benign samples in which cases yielding high than 10 fold relative SLC45A3-ELK4 mRNA levels are indicated in dark red. Relative levels of SLC45A-ELK4 mRNA in 10 cancer cell lines and 1 benign kidney cell line compared to the benign prostate epithelial cell line RWPE-1 is to the right. 1*c*. Schematic of the sequencing results obtained from amplified (primers are indicated by arrows) and gel extracted cDNA from PCR and 5'RACE (primer is indicated by the arrow) that correspond to the different SLC45A3-

ELK4 cDNA variants (v) which are described as follows: variant 1: SLC45A3 (exon 1)-ELK4 (exon 2); variant 2: SLC45A3 (exon 1-2)-ELK4 (exon 2); variant 3: SLC45A3 (truncated exon 2)-ELK4 (exon 2); variant 4: SLC45A3 (exon 1, beginning of exon 2-end of exon 4)-84 base pair intergenic sequence between SLC45A3 and ELK4-ELK4 (exon 2); variant 5: SLC45A3 (exon 1-4)-intergenic sequence between SLC45A3 and ELK4-ELK4 (exon 2). 1d. Bar chart shows TAQMAN assay (described in FIGS. 1a and 1b) results from RNA extracted from 6 urine samples. Raw values for SLC45A3-ELK4 were normalized to the control gene TCFL1 and then calibrated to 1 of the cases yielding negative cancer results on biopsy material. Shown are relative mRNA from the other 5 samples (C08, C03, C33 and C30 corresponding to cancer positive biopsies and C13 corresponded to cancer negative biopsy).

Figure 1B:
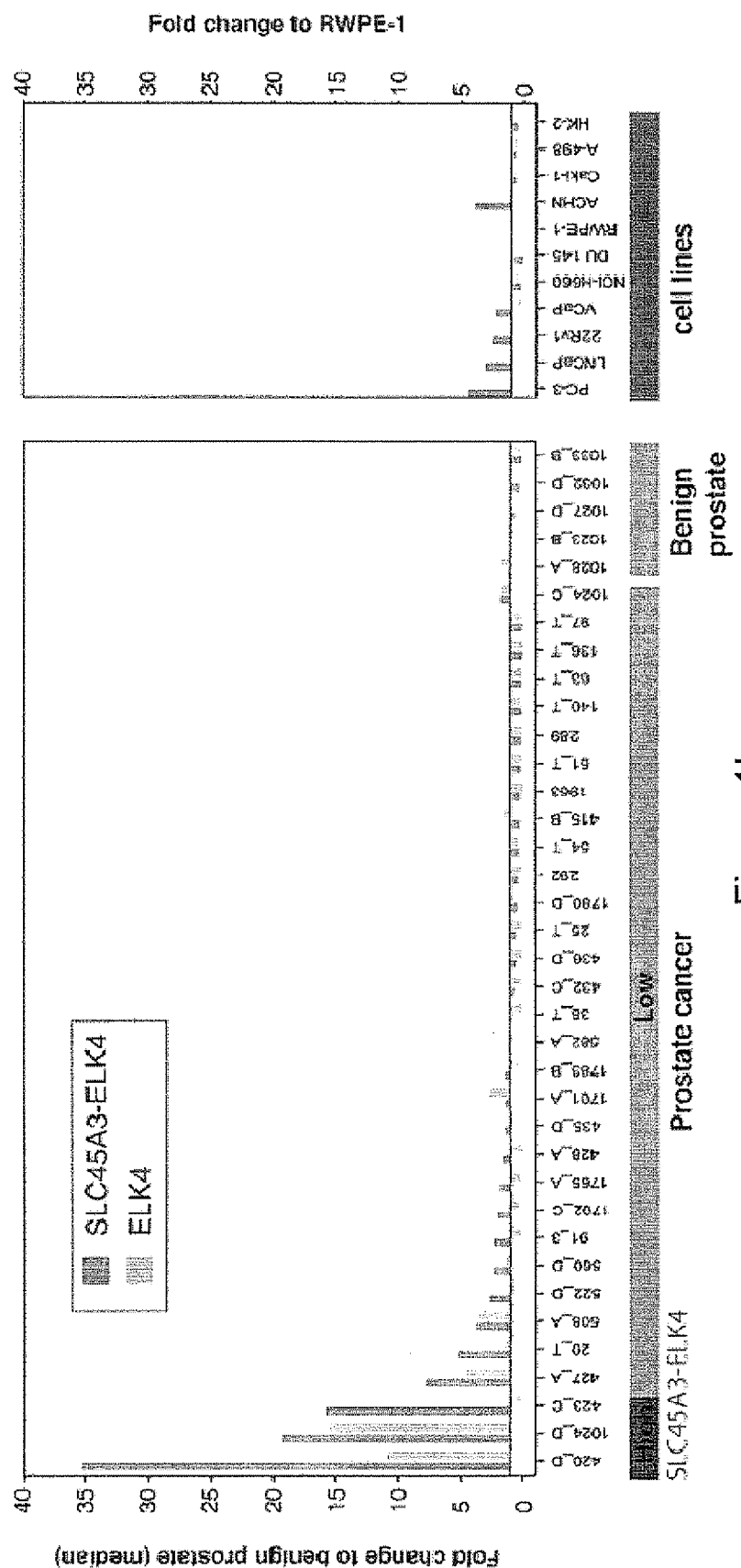
Figure 1C:
Figure 1C:
Figure 1C:
Figure 1C:
Figure 1C:
Figure 2:
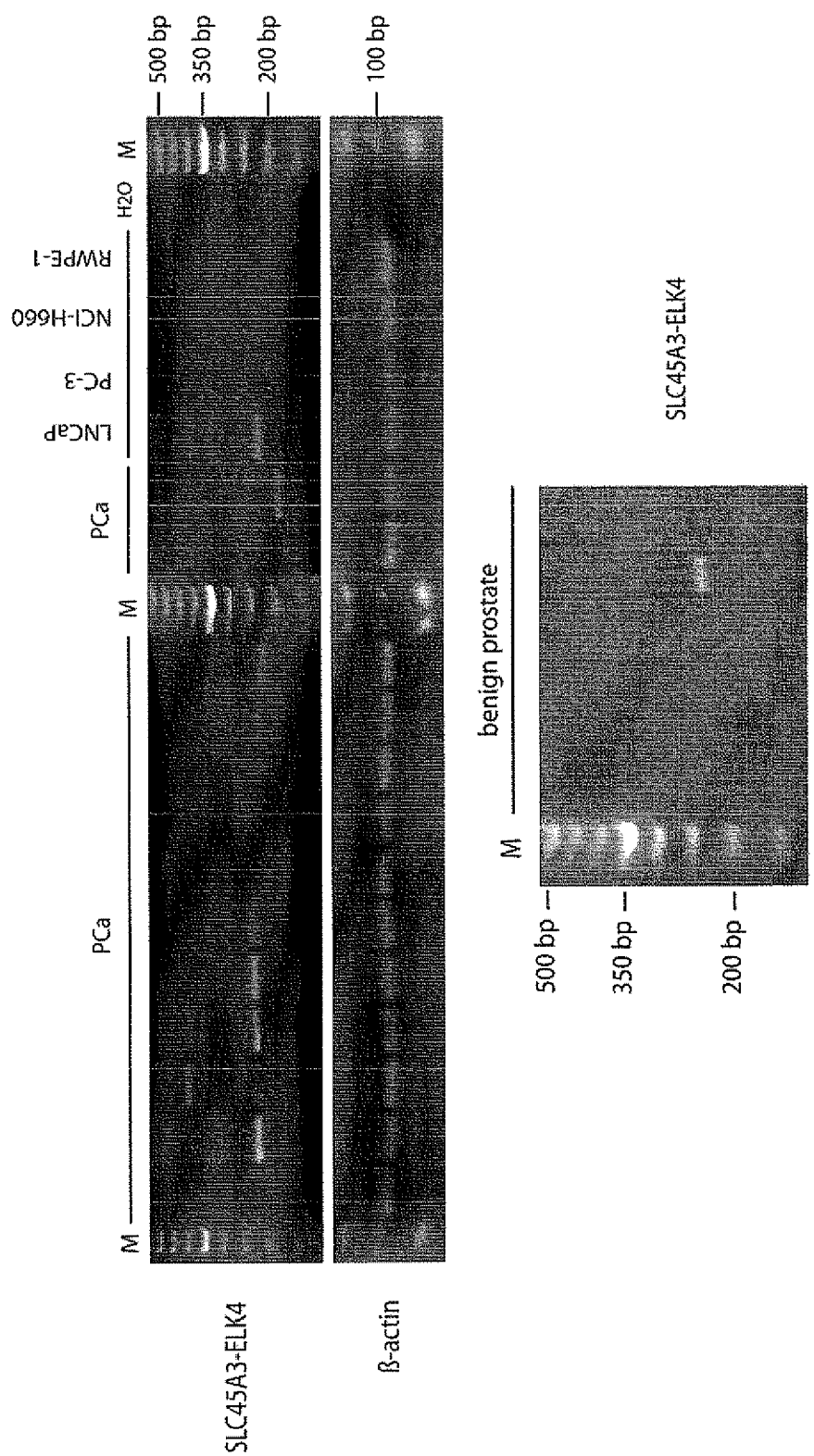

FIG. 2. Conventional PCR results. Using primers indicated in FIG. 1c, RT-PCR was performed on total RNA extracted from 35 prostate cancer samples, 6 benign samples, 6 prostate cancer cell lines (NCI-H660, VCaP, PC3, LNCaP, DU145, 22-Rv1) and 1 benign cell line (RWPE-1). This gel shows representative bands from prostate cancer samples (PCa) and NCI-H660, VCaP, PC3, LNCaP and RWPE-1 cells.

Figure 3:
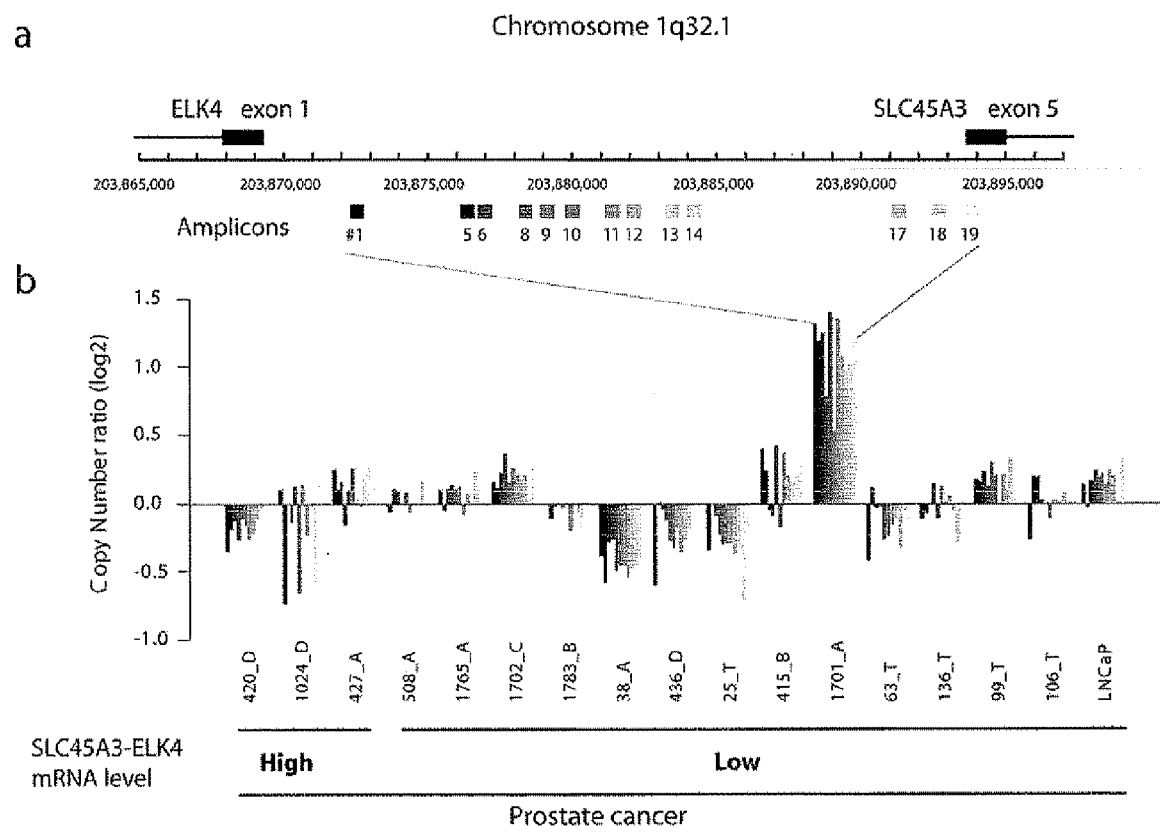

FIGS. 3a-3b. Genomic characterization of the chromosome 1 region separating SLC45A3 and ELK4. 3a. Schematic of the region Chr.1q32 demonstrating the position of the primer pairs that were specific to each of the 13 amplicons. SLC45A3 exon 5 and ELK4 exon 1 positions are indicated. 3b. Quantitative PCR (Q-PCR) results obtained from each of the 13 amplicons obtained for 16 prostate cancer samples (ordered from left to right as a function of the level of SLC45A3-ELK4 mRNA measured by the described TAQMAN assay) and from LNCaP cells. The prostate cancer samples are divided into 2 groups those with over 10-fold higher ("High") or similar ("Low") SLC45A3-ELK4 mRNA levels compared to benign samples. All Q-PCR experiments were run in triplicate. Bars indicate the average normalized values that have been normalized to another region on chromosome 1q that is not altered.

Figure 4:
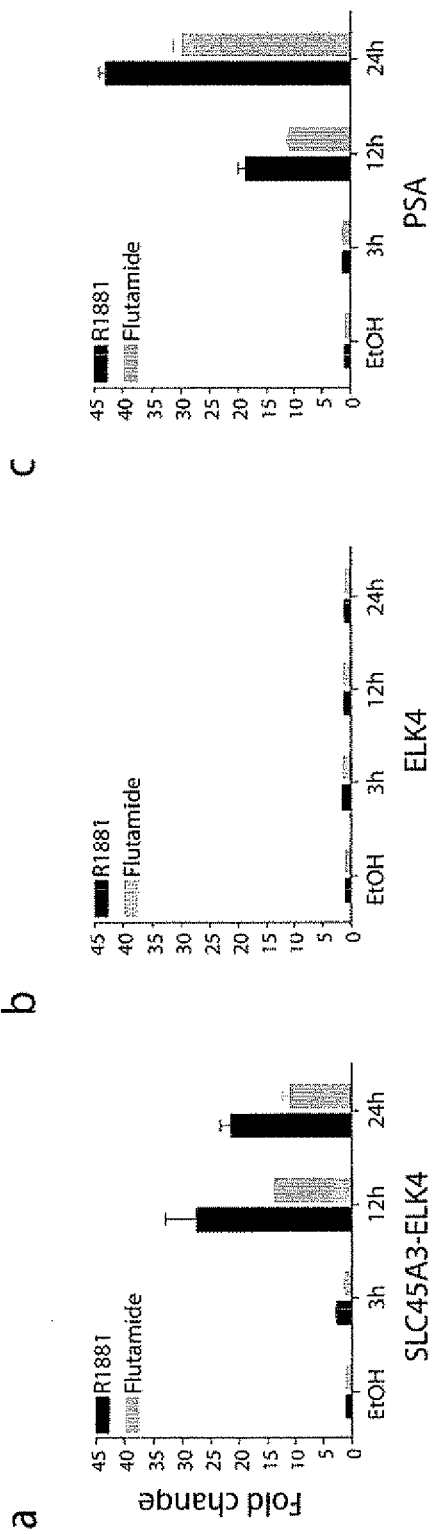

FIGS. 4a-4c. Androgen stimulation of LNCaP cells and induction of SLC45A3-ELK4 (FIG. 4a), endogenous ELK4 (FIG. 4b) mRNA and KLK3 (PSA) mRNA (FIG. 4c). Bar charts are the average fold induction in LNCaP cells treated with 1nM R1881 in the absence (black bars) or presence (gray bars) of 10 μM flutamide at the indicated time points. For flutamide treatment cells were pre-treated 2 hours with 10 μM flutamide, medium was removed and the fresh medium plus 1 nM R1881 plus 10 μM flutamide were given for the indicated time points. All experiments were run in triplicates (standard deviation indicated by the error bars).

DETAILED DESCRIPTION OF THE INVENTION

Expression of SLC45A3-ELK4 fusion transcripts, particularly expression of SLC45A3-ELK4 fusion transcripts, has been shown to occur at high levels in prostate cancer tissue and in urine samples from men at risk for prostate cancer. Several SLC45A3-ELK4 fusion transcript variants have been identified and have been shown to be androgen-regulated. Disclosed herein are compositions and methods useful for diagnosing cancer, particularly prostate cancer, based on detection of SLC45A3-ELK4 fusion molecules. Additional drug screening and therapeutic methods are also provided.

SLC45A3-ELK4 Fusion Molecules

Disclosed herein are embodiments of SLC45A3-ELK4 fusion transcripts (i.e., mRNAs) that are detected in subjects with prostate cancer. These fusion transcripts are believed to result from an event that is distinguishable from a chromosomal rearrangement as seen for other ETS fusion events in prostate cancer. Without being bound to any particular theory, these SLC45A3-ELK4 fusion transcripts could be a result of trans-splicing, genomic rearrangement, or a combination of both mechanisms. Upon translation, the fusion transcripts produce fusion proteins.

The term "SLC45A3-ELK4 fusion molecule", as used herein, can be a chimeric nucleic acid molecule (genomic DNA, cDNA, and RNA) or a chimeric protein molecule.

For example, a SLC45A3-ELK4 fusion transcript or mRNA molecule is composed of at least a 5' portion of a SLC45A3 mRNA, joined 5' to at least a 3' portion of an ELK4 mRNA. A SLC45A3-ELK4 fusion transcript may also include a sequence from the intergenic region between the SLC45A3 gene and the ELK4 gene. The SLC45A3 cDNA and two ELK4 cDNA (corresponding to two splice variants) sequences are set forth in SEQ ID NOS: 6-8.

The 5' portion of a SLC45A3 mRNA that constitutes a fusion transcript may include the 5' un-translated region of a SLC45A3 mRNA. The 5' un-translated region of an mRNA starts at the +1 position (i.e., where transcription begins) and ends just before the start codon of the coding region.

The 5' portion of a SLC45A3 mRNA that constitutes a fusion transcript also includes full length or portions of one or more exons of a SLC45A3 mRNA. The five exons of the human SLC45A3 mRNA are shown in SEQ ID NO: 6.

By a "portion" of an exon, it is meant a contiguous sequence of an exon that is shorted than the entire length of the exon. Generally speaking, a portion of an exon can be at least 5, 10, 15, 20, 25, 30, 35, 40 nucleotides or more in length.

In one embodiment, the fusion transcript includes at least exon 1 of SLC45A3, or a portion of exon 1. In another embodiment, the fusion transcript includes at least exon 1 of SLC45A3, or a portion thereof, along with full or parts of one or more downstream exons of SLC45A3 (i.e., exons 2, 3, 4 and 5).

The 3' portion of an ELK4 mRNA that constitutes a fusion transcript may include the 3' un-translated region transcribed from the ELK4 gene. The 3' un-translated region is the section of an mRNA that follows the coding region and is not translated. The 3' un-translated region is typically followed by a poly A tail.

The 3' portion of an ELK4 mRNA that constitutes a fusion transcript can also include full length or portions of one or more exons from the 3' of an ELK4 mRNA, such as exon 5, exon 4, exon 3a, exon 3b, and exon 2, or portions thereof. The exons of two splice variants of human ELK4 cDNA are shown in SEQ ID NOS: 7-8.

In a specific embodiment, a SLC45A3-ELK4 fusion transcript is composed of a 5' portion of a SLC45A3 mRNA which includes at least exon 1 of the SLC45A3 mRNA, joined 5' to a 3' portion of an ELK4 mRNA which includes exon 2 or a portion thereof and one or more of the downstream exons of the ELK4 mRNA. An example of such fusion transcript is Variant 1 described in the Examples below, having the junction sequence set forth in SEQ ID NO: 1.

In another embodiment, a SLC45A3-ELK4 fusion transcript is composed of a 5' portion of a SLC45A3 mRNA which includes exon 1 and a portion of exon 2 of the SLC45A3 mRNA, joined 5' to a 3' portion of an ELK4 mRNA which includes exon 2 or a portion thereof and the downstream exons of the ELK4 mRNA. Examples of such fusion transcript are Variant 2 and Variant 3 described in the Examples below, having the junction sequences set forth in SEQ ID NO: 2 and SEQ ID NO: 3, respectively.

In still another embodiment, a SLC45A3-ELK4 fusion transcript is composed of a 5' portion of a SLC45A3 mRNA which includes exon 1, a portion of exon 2, and a portion of exon 4 of the SLC45A3 mRNA, joined 5' to a 3' portion of an ELK4 mRNA which includes exon 2 or a portion thereof and the downstream exons of the ELK4 mRNA. An example of such fusion transcript is Variant 4 described in the Examples below, having its junction sequence shown in SEQ ID NO: 4.

In yet another embodiment, a SLC45A3-ELK4 fusion transcript is composed of a 5' portion of a SLC45A3 mRNA which includes at least a portion of exon 3 and exon 4 of the SLC45A3 mRNA, joined 5' to a 3' portion of an ELK4 mRNA which includes exon 2 or a portion thereof and the downstream exons of the ELK4 mRNA. An example of such fusion transcript is Variant 5 described in the Examples below, having its junction sequence shown in SEQ ID NO: 5.

Upon translation, the fusion transcripts produce fusion proteins. Because formation of the fusion transcript may cause frame shift, the amino acids encoded by the ELK4 mRNA portion of the fusion transcript may or may not correspond to those originally encoded by the 3' portion of the ELK4 mRNA.

Basis of Diagnosis

According to the present invention, diagnosis of cancer in a subject is based on detection of SLC45A3-ELK4 fusion molecules in a sample. Elevated expression of SLC45A3-ELK4 fusion transcripts have been specifically shown to occur in subjects with prostate cancer and are believed to occur in other cancers as well. Hence the method provided by the present invention is applicable to diagnosing cancer, including but not limited to prostate, breast, colon, pancreas, and lung cancers.

The term "subject" being tested includes all mammalian subjects, particularly human subjects.

The term "diagnosis" or "diagnosing" is meant a determination that the subject has cancer or likely has cancer. The diagnostic method based on detection of SLC45A3-ELK4 fusion molecules can be combined with other diagnostic tests to reduce false positive or false negative results.

Sample sources suitable for use in the detection include any biological specimen that contains fusion molecules for detection as described herein. Examples include tissue, urine, blood, semen, prostatic secretions or prostate cells. In a specific embodiment, a urine sample is collected immediately following a digital rectal examination (DRE), which often causes prostate cells from the prostate gland to shed into the urinary tract. Samples obtained from the above-identified sources can be further processed in order to enrich for the fusion molecules or cells containing the fusion molecules. The processing may include obtaining the serum or plasma portion of blood, obtaining the supernatant or cell pellet portion of urine, homogenization of tissue, lysis of cells, among others, in order to provide materials suitable for assaying the fusion molecules.

Diagnosis of cancer can be based on detection of the presence of a fusion molecule at an elevated level. Alternatively or additionally, diagnosis can be based on detection of elevated levels of a specific fusion molecule based on the composition or identity of the specific fusion molecule.

By "elevated level" is meant the level is significantly increased as compared to control level, i.e., levels of fusion observed in normal tissue (e.g., normal or benign prostate tissue, and/or normal non-prostate tissue). A significant increase is meant an increase by at least 50%, 75%, 100% (twice the normal level), 2 fold, 3 fold, 4 fold, 5 fold, 6 fold, 7 fold, 8 fold, 9 fold, 10 fold, 11 fold, 12 fold, 13 fold, 14 fold, 15 fold, or greater.

For example, SLC45A3-ELK4 fusion transcripts can be detected by RT-PCR using primers including a first primer which corresponds to or is specific for the sequence of a 5' portion of a SLC45A3 mRNA (such as exon 1), and a second primer specific for or corresponding to the sequence of a 3' portion of an ELK4 mRNA (such as exon 2 or any other downstream exon). A positive signal represents the presence of one or more SLC45A3-ELK4 fusion transcript variants, or a combination of different variants. Quantitation of the level (or signal) and comparison to levels in normal tissue will provide the basis for diagnosis.

When referring to an oligonucleotide primer or probe as "corresponding to" or "specific for" a sequence, it is meant that such primer or probe has sufficient identity with the sequence such that the primer or probe specifically hybridizes to the sequence or its complementary strand under stringent conditions. Stringency is dictated by temperature, ionic strength, and the presence of other compounds such as organic solvents. For example, "high stringency conditions" can encompass hybridization at 42° C. in a solution consisting of 5×SSPE (43.8 g/l NaCl, 6.9 g/l NaH2PO4H2O and 1.85 g/l EDTA, pH adjusted to 7.4 with NaOH), 0.5% SDS, 5×Denhardt's reagent and 100 µg/ml denatured salmon sperm DNA, followed by washing in a solution comprising 0.1×SSPE, 1.0% SDS at 42° C. or higher. "Medium stringency conditions" can encompass hybridization at 42° C. in a solution consisting of 5×SSPE with NaOH), 0.5% SDS, 5×Denhardt's reagent and 100 µg/ml denatured salmon sperm DNA followed by washing in a solution comprising 1.0×SSPE, 1.0% SDS at 42° C.

Oligonucleotide primers or probes suitable for use in the detection can include additional features in addition to the sequence binding region, such as a sequence that does not bind to the junction sequence (e.g., a tag sequence or a promoter sequence) and does not interfere with binding to the intended target sequence in the junction. Similarly, the primers or probes can include non-nucleic acid moieties such as labels that do not interfere with target binding.

In addition or as an alternative to detecting the presence of a (i.e., any) SLC45A3-ELK4 fusion molecule, a specific fusion molecule can also be detected based on the composition or identity of the specific fusion molecule. For example, RT-PCR products obtained using a first primer corresponding to a 5' portion of a SLC45A3 mRNA and a second primer corresponding to a 3' portion of an ELK4 mRNA, can be evaluated on an agarose to identify the sizes of the RT-PCR products. The junction of Variant 1 exemplified herein, which includes exon 1 of SLC45A3 and exon 2 of ELK4, is 325 bp (SEQ ID NO: 1), whereas the junctions for Variants 2-5 as shown in FIG. 1c and SEQ ID NOS: 2-5 are 615, 379, 371, and 774 bp, respectively. RT-PCR products can also be sequenced to determine the identity of the fusion transcript(s). Alternatively, primers or probes specifically designed based on the junction sequences of identified variants can be used in hybridization or amplification based assays such as RT-PCR, FISH, among others, in order to determine the presence and level of specific fusion transcript variants.

To illustrate, SEQ ID NOS: 1-5 set forth the junction sequences of five fusion transcript variants, with points of junctions indicated by asterisks and with shared nucleotide(s) between SLC45A3 and ELK4 shown by underline:

```
Variant 1: SLC45A3 (exon 1)-ELK4 (exon 2)
                                         (SEQ ID NO: 1)
AACCTGGAGATTTAAAAGCCGCCGGCTGGCGCGCGTGGGGGGCAAG
GAAGGGGGGCGGAACCAGCCTGCACGCGCTGGCTCCGGGTGACAG
CCGCGCGCCTCGGCCA*G*CTCATTGCTATGGACAGTGCTATCACC
CTGTGGCAGTTCCTTCTTCAGCTCCTGCAGAAGCCTCAGAACAAGC
ACATGATCTGTTGGACCTCTAATGATGGGCAGTTTAAGCTTTTGCA
GGCAGAAGAGGTGGCTCGTCTCTGGGGGATTCGCAAGAACAAGCCT
AACATGAATTATGACAAACTCAGCCGAGCCCTCAGATACTATTATG
TAAAG Variant 2: SLC45A3 (exon 1-SLC45A3 (beginning
of exon 2-ELK4 (exon 2)
                                         (SEQ ID NO: 2)
AACCTGGAGATTTAAAAGCCGCCGGCTGGCGCGCGTGGGGGGCAAG
GAAGGGGGGCGGAACCAGCCTGCACGCGCTGGCTCCGGGTGACAG
CCGCGCGCCTCGGCCAGGATCTGAGTGATGAGACGTGTCCCCACTG
AGGTGCCCCACAGCAGCAGGTGTTGAGCATGGGCTGAGAAGCTGGA
CCGGCACCAAAGGGCTGGCAGAAATGGGCGCCTGGCTGATTCCTAG
GCAGTTGGCGGCAGCAAGGAGGAGAGGCCGCAGCTTCTGGAGCAGA
GCCGAGACGAAGCAGTTCTGGAGTGCCTGAACGGCCCCTGAGCCC
TACCCGCCTGGCCCACTATGGTCCAGAGGCTGTGGGTGAGCCGCCT
GCTGCGGCACCGGAAAGCCCAGCTCTTGCTGGTCAACCTGCTAACC
TTTGGCCTGGAGGTGTGTTTGGCCGCAGGCATCACCTATGTGCCGC
CTCTGCTGCTGGAAGTGGGGGTAGAGGAGAAGTTCATGACCATGGT
GCTG*GCTCATTG*CTATGGACAGTGCTATCACCCTGTGGCAGTTC
CTTCTTCAGCTCCTGCAGAAGCCTCAGAACAAGCACATGATCTGTT
GGACCTCTAATGATGGGCA Variant 3: SLC45A3 (exon 1-SLC45A3 (beginning
of exon 2-SLC45A3 (end of exon 2)- ELK4
(exon 2)
                                         (SEQ ID NO: 3)
AACCTGGAGATTTAAAAGCCGCCGGCTGGCGCGCGTGGGGGGCAAG
GAAGGGGGGCGGAACCAGCCTGCACGCGCTGGCTCCGGGTGACAG
CCGCGCGCCTCGGCCAGGATCTGAGTGATGAGACGTGTCCCCACTG
AGGTGCCCCACAGCAGCTCTTGCTGGTCAACCTGCTAACCTTTGGC
CTGGAGGTGTGTTTGGCCGCAGGCATCACCTATGTGCCGCCTCTGC
TGCTGGAAGTGGGGGTAGAGGAGAAGTTCATGACCATGGTGCTG*G
CTCATTG*CTATGGACAGTGCTATCACCCTGTGGCAGTTCCTTCTT
CAGCTCCTGCAGAAGCCTCAGAACAAGCACATGATCTGTTGGACCT
CTAATGATGGGCA Variant 4: SLC45A3 (exon 1-SLC45A3 (beginning
of exon 2-SLC45A3 (end of exon 4-intergenic
sequence between SLC45A3 and ELK4-ELK4
(exon 2)
                                         (SEQ ID NO: 4)
AACCTGGAGATTTAAAAGCCGCCGGCTGGCGCGCGTGGGGGGCAAG
GAAGGGGGGCGGAACCAGCCTGCACGCGCTGGCTCCGGGTGACAG
CCGCGCGCCTCGGCCAGGATCTGAGTGATGAGACGTGTCCCCACTG
AGGTGCCCCTACAC*ACTGGCCTCCCTCTACCACCGGGAGAAGCAG
*TGGAGGACTTTTACCCGTCTCCTCACCTTCTGATACACACCAACC
AACCAGGTCAACCAGCCATTGCTGTTTACTGGATACCT*GCTCATT
GCTATGGACAGTGCTATCACCCTGTGGCAGTTCCTTCTTCAGCTCC
TGCAGAAGCCTCAGAACAAGCACATGATCTGTTGGACCTCTAATGA
TGGGCA Variant 5: SLC45A3 (end of exon 3-SLC45A3
(exon 4-intergenic sequence between SLC45A3
and ELK4-ELK4 (exon 2) from 5' RACE.
                                         (SEQ ID NO: 5)
TGGGCCCCACCGAGCCAGCAGAAGGGCTGTCGGCCCCCTCCTTGTC
GCCCCACTGCTGTCCATGCCGGGCCCGCTTGGCTTTCCGGAACCTG
GGCGCCCTGCTTCCCCGGCTGCACCAGCTGTGCTGCGCATGCCCC
GCACCCTGCGCCGGCTCTTCGTGGCTGAGCTGTGCAGCTGGATGGC
ACTCATGACCTTCACGCTGTTTTACACGGATTTCGTGGGCGAGGGG
CTGTACCAGGGCGTGCCCAGAGCTGAGCCGGGCACCGAGGCCCGGA
GACACTATGATGAAGGCGTTCGGATGGGAGCCTGGGGCTGTTCCTG
CAGTGCGCCATCTCCCTGGTCTTCTCTCTGGTCATGGACCGGCTGG
TGCAGCGATTCGGCACTCGAGCAGTCTATTTGGCCAGTGTGGCAGC
TTTCCCTGTGGCTGCCGGTGCCACATGCCTGTCCCACAGTGTGGCC
GTGGTGACAGCTTCAGCCGCCCTCACCGGGTTCACCTTCTCAGCCC
TGCAGATCCTGCCCTACACACTGGCCTCCCTCTACCACCGGGAGAA
```

-continued
```
GCAG*TGGAGGACTTTTGACCCGTCTCCTCACCTTCTGATACACAC
CAACCAACCAGTCAACCAGCCATTGCTGTTTACTGGATACCT*GCT
CATTGCTATGGACAGTGCTATCACCCTGTGGCAGTTCCTTCTTCAG
CTCCTGCAGAAGCCTCAGAACAAGCACATGATCTGTTGGACCTCTA
ATGATGGGCAGTTTAAGCTTTTGCAGGCAGAAGAGGTGG.
```

A fusion transcript may include several junctions that are not normally observed in native SLC45A3 or ELK4 mRNAs. See, e.g., Variants 4 and 5. To detect a specific fusion transcript, a primer or probe can be designed based on the sequence surrounding a point of junction. Such primers are also referred to herein as a "junction-specific" primer.

Generally speaking, a junction-specific oligonucleotide primer or probe should be at least about 14 or 15 nucleotides in length, or 16, 17, 18, 19, 20, 21, 22, 23, 24, 25 or more nucleotides in length. A junction-specific oligonucleotide primer or probe is designed to have sufficient identity to a junction such that it hybridizes specifically to the junction under stringent conditions. In specific embodiments, a junction specific primer or probe includes at least 3, 5, 6, 7, 8, 9, 10, 11, or 12 nucleotides from either side of the point of junction. If a fusion junction contains one or more nucleotides that are common to the two joining nucleic acids, a junction-specific primer should include the shared or common nucleotide or nucleotides, and additionally, at least 3, 5, 6, 7, 8, 9, 10, 11, or 12 nucleotides from either side of the shared nucleotide(s). In other embodiments, especially for amplification-based detection, a junction-specific primer is designed to target more of the 5' partner of the fusion than the 3' partner to minimize hybridization of the primer to native, non-fusion SLA45A3 or ELK4 mRNA. In other words, the primer has a bigger 5' portion that hybridizes to one side of the junction sequence than the 3' portion of the primer which hybridizes to the other side of the junction. For example, a junction specific primer of 18 nucleotides in length can include a 5' portion of 12-14 nucleotides that corresponds to one side of the junction sequence, and a 3' portion of 4-6 nucleotides that corresponds to the other side of the junction sequence.

In specific embodiments, junction-specific primers are designed based on the junction where a SLC45A3 portion and an ELK4 portion are fused.

In one embodiment, a junction specific primer is designed based on the junction sequence of Variant 1 (SEQ ID NO: 1). In a specific embodiment, the primer contains at least 14 to 18 nucleotides, and includes at least 4 or 5 nucleotides of SLC45A3 exon 1 right before the "G" nucleotide at the point of junction of Variant 1, and at least 4 or 5 nucleotides of ELK4 exon 2 right after the "G" nucleotide at the point of junction.

In other embodiments, junction specific primers are designed based on the junction sequences of Variants 2-3 (SEQ ID NOS: 2-3). In a specific embodiment, the primer contains at least 14 to 18 nucleotides, and includes at least 3 or 4 nucleotides of SLC45A3 exon 2 right before the shared "GCTCATTG" segment at the point of junction of Variant 2 or 3, and at least 3 or 4 nucleotides of ELK4 exon 2 immediately after the shared segment at the point of junction.

Similarly, peptides specifically designed based on the junction amino acid sequences of identified variants can be used to generate antibodies usefully for detecting the presence and level of specific fusion protein variants.

As described above, the diagnostic method based on detection of SLC45A3-ELK4 fusion molecules can be combined with other tests in order to achieve more accurate diagnostic results. Other diagnostic tests include, for example, detection of other fusions associated with cancer, including gene fusions associated with prostate cancer, e.g., gene fusions between the androgen-regulated transmembrane protease, serine 2 (TMPRSS2) gene and a gene of the ETS family of transcription factors (e.g., ERG), as described in U.S. Published Application 2007/0212702; and fusion between the SLC45A3 gene and the ERG gene. In the experiments described in the following examples, no mutually exclusive expression has been observed between TMPRSS2-ERG gene fusion and SLC45A3-ELK4 fusion transcripts. In addition, several samples that yielded high SLC45A3-ELK4 transcript levels were negative for ERG rearrangement. Accordingly, detection of SLC45A3-ELK4 fusion molecules may provide a useful complement of diagnostic tests based on detection of fusions involving ERG, including TMPRSS2-ERG gene fusion.

Techniques and Assays for Detection of Fusion Molecules

Fusion nucleic acid molecules can be detected by using a variety of known nucleic acid-based techniques, including hybridization (such as solution-phase hybridization, in situ hybridization (ISH), e.g., fluorescent ISH (FISH); microarray, Northern blot and Southern blot), amplification (such as polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA)), and sequencing.

Fusion proteins can be detected based on detecting a variety of assays known for detection of proteins, including, for example, immunoassays (such as immunoprecipitation, Western blot, ELISA, immunohistochemistry, immunocytochemistry, and flow cytometry).

Compositions and Kits

The present invention also provides compositions and kits for use in the diagnostic methods described above, including, for example, primers or primer pairs suitable for use in amplification, probes suitable for use in hybridization, including junction-specific primers and probes, and antibodies. Primer pairs can include a junction-specific primer and non-junction-specific primer. Primers and probes can be labeled with an agent or compound that generates a detectable signal, or immobilized on a solid support.

Additional Utilities

In a further embodiment, the invention provides a method of screening for an anti-cancer compound. Specifically, candidate compounds are screened for their ability to reduce the level of expression or inhibit a biological function of a SLC45A3-ELK4 fusion molecule in a cancerous cell. The method can be performed in vitro using a cancerous cell line shown to have elevated levels of a SLC45A3-ELK4 fusion molecule. Candidate compounds can include nucleic acid molecules, small organic molecules, and antibodies, for example. The identified compound may reduce either the mRNA or the protein level of a fusion molecule.

In another embodiment, the invention provides a method of treating a cancer characterized by elevated levels of a SLC45A3-ELK4 fusion molecule. The elevated levels of a fusion molecule may be detected either in a specific tissue or organ, and/or in the blood or urine sample. The treatment involves administration to the cancer patient an agent that inhibits a biological function of the fusion molecule, or reduces the level of the fusion molecule. The agent can be any one of a small molecule, an siRNA, an antisense nucleic acid, or an antibody, or a combination thereof. siRNAs refers to small interfering RNAs, which may include a double-stranded region of about 18-30, or 20-25 nucleotides. One strand of the double-stranded region is identical or substantially homologous to a target RNA molecule. The double-stranded region can be formed by two separate RNA strands, or a singled RNA molecule (i.e., a hairpin shape). In one embodiment, the anti-cancer agent contains an siRNA designed to target the junction region of a SLC45A3-ELK4 fusion transcript.

In the following examples, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that changes may be made without departing from the scope of the present invention. The following description of exemplified embodiments is, therefore, not to be taken in a limited sense, and the scope of the present invention is defined by the appended claims.

EXAMPLES

In the following Examples all cell lines were obtained from American Type Culture Collection (ATCC®, Manassas, Va.). Cells were maintained according to the supplier's instructions. Tissue samples were processed and RNA was extracted as follows: Hematoxylin and eosin (H&E) slides were evaluated for cancer extent and tumor grade (Gleason Score). Areas with high-density cancer foci (<10% stromal and other non-tumor tissue contamination) were cored using a 1.5 mm dermatome from the corresponding frozen tissue block. RNA was isolated using TRIzole® Reagent (Invitrogen, Carlsbad, Calif.) according to the manufacturer's instructions. RNA was then subjected to DNase treatment (Invitrogen) and quantified using a NanoDrop 8000 spectrophotometer (Thermo Scientific, Wilmington, Del.). The quality of RNA was then measured using the Bioanalyzer 2100 (Agilent Technologies Inc., Santa Clara, Calif.).

Example 1

SLC45A3-ELK4 mRNA was Expressed in Prostate Cancer, Benign Prostate Tissue and the LNCaP Cancer Line A TAQMAN assay was designed to screen for the expression of a putative SLC45A3-ELK4 transcript. This assay targets SLC45A3 exon 1 and ELK4 exon 2 based on fusion junctions between SLC45A3 and ETV1 and ETV5 (FIG. 1a) keeping in mind the differences in the 3' regions of the 2 known wild type ELK4 mRNA variants (NM_001973 and NM_021795). Initially RNA was screened from 31 prostate cancer tissue samples, 6 benign prostate tissue samples and 11 cell lines including malignant prostate (LNCaP, PC-3, 22Rv1, VCaP, NCI-H660, DU-145), non-prostate (human epithelial-like kidney adenocarcinoma cell line ACHN, Caki-1, A-498, HK-2) and non-malignant prostate (RWPE-1) epithelial cell lines. Almost all samples yielded detectable, albeit low, SLC45A3-ELK4 mRNA transcript expression (FIG. 1b). Three prostate cancer samples demonstrated high SCL45A3-ELK4 expression with levels greater than 10-fold over the mean level calculated from benign prostate tissue. The remainder of the prostate cancer samples demonstrated low SLC45A3-ELK4 mRNA levels similar to the benign tissue samples. Levels of endogenous ELK4 mRNA varied widely in all prostate samples tested. While a good overall correlation was found between endogenous ELK4 mRNA and SLC45A3-ELK4 mRNA levels (r=0.86), several samples yielded significantly different expression values between the 2 transcripts (e.g. samples 423_C, 20_T, 522_D, 91_T, 1702_C, 1765_A, 428_A and 1701_A). Relatively increased levels of SLC45A3-ELK4 were found in PC-3 and LNCaP cells and the human epithelial-like kidney adenocarcinoma cell line ACHN.

Example 2

SLC45A3-ELK4 mRNA Variants were Detected in Prostate Cancer

In order to characterize the composition of the SLC45A3-ELK4 transcripts, primers to SLC45A3 exon 1 and ELK4 exon 2 were used to perform conventional RT-PCR followed by cDNA sequencing of amplified products obtained from 35 prostate cancer samples, 6 benign samples, 6 prostate cancer cell lines (NCI-H660, VCaP, PC3, LNCaP, DU145, 22-RV1) and 1 benign cell line (RWPE-1). See FIG. 2. Given the lower sensitivity of this approach only the majority of the samples yielded a major product that consisted of SLC45A3 exon 1 fused to ELK4 exon 2 (FIG. 1c, see junction sequence of Variant 1 below). Three less common products were detected consisting of different exons of SLC45A3 fused to ELK4 exon 2. One unexpected amplified product was found that consisted of complete or parts of SLC45A3 exons 1, 2, and 4 fused to 84 base pairs from a chromosome 1 region that separates SLC45A3 and ELK4, and then followed by ELK4 exon 2 (Variant 4). To confirm the expression of SLC45A3-ELK4 mRNA using an unbiased approach, 5' RNA ligase-mediated rapid amplification of cDNA ends (RACE) was performed on sample 1701_A. Another SLC45A3-ELK4 mRNA variant consisting of SLC45A3 exons 1-3 fused to the same 84-bp sequence described above followed by ELK4 exon 2 was also identified (Variant 5). Unlike the other fusions characterized in prostate cancer, SLC45A3-ELK4 fusions represented by these data are heterogeneous, in which some fusions may harbour an intergenic chromosome sequence within the fusion transcript.

Conventional RT-PCR. The qualitative detection of SLC45A3-ELK4 transcripts was performed using Platinum Taq DNA Polymerase kit (Invitrogen) and 50 ng of cDNA as template in a final volume of 25 μl. The PCR was run using a forward primer in SLC45A3 exon 1 (5'-CCGCG-GAGTAACCTGGAGATTT-3', SEQ ID NO: 37) and reverse primer in ELK4 exon 2 (5'-TGCCCATCATTAGAG-GTCCAACAG-3', SEQ ID NO: 38) under the following cycling conditions (94° C. 2 min initial denaturation, 94° C. 30 sec, 56° C. 30 sec, 68° C. 1 min, for 40 cycles and 68° C. 10 min final extension). The amplicons were separated on a 2.5% agarose gel.

cDNA Sequencing. DNA fragments corresponding to the expected sizes of fusion transcripts were gel extracted using the MinElute™ Gel Extraction Kit (Qiagen) and sequenced at the Life Sciences Core Laboratories Center's DNA sequencing facility of Cornell University (Ithaca, N.Y.).

Example 3

Figure 1D:
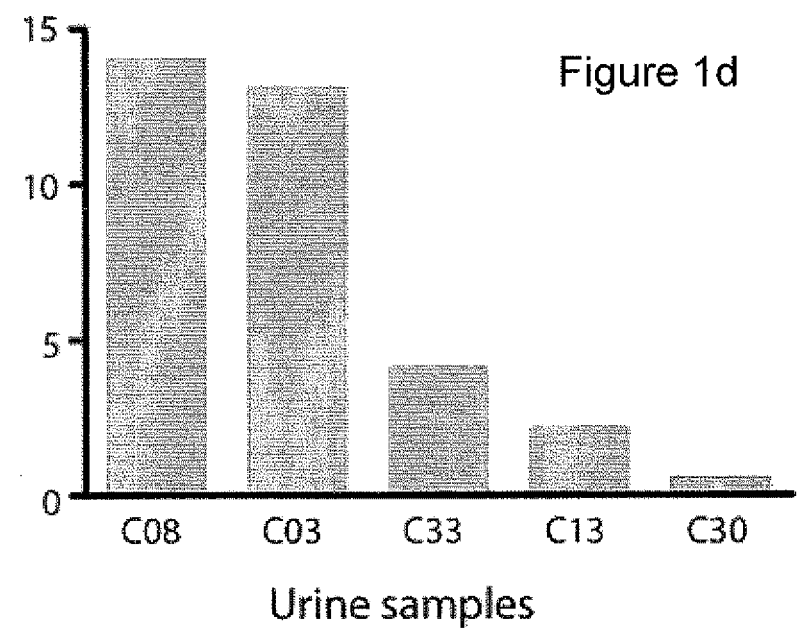

SLC45A3-ELK4 mRNA can be Detected Using a Non-Invasive Assay 14 pre-biopsy, post-digital exam urine specimens from men who were at risk for having prostate cancer were examined using the described SLC45A3-ELK4 TAQMAN assay. According to pathology reports of the biopsied prostate tissue, 8 out of the 14 were diagnosed with prostate cancer (FIG. 1d). Detectable levels of SLC45A3-ELK4 transcript were measured in 6 out of 8 corresponding urine specimens and 2 out of the 6 specimens from men whose biopsies did not reveal prostate cancer yielding a sensitivity of 75% and a specificity of 67%. Interestingly, as seen in the prostate tissue, high levels (>10-fold) were detected in only a few of the prostate cancer-associated samples. Table 1 below is a contingency table of all 14 samples analyzed and that yielded adequate values for TCFL1. Based on this table, a sensitivity of 75% and a specificity of 67% were determined for the SLC45A3-ELK4 detection in the urine as a biomarker for prostate cancer diagnosed based on biopsy material.

TABLE 1

| Prostate Cancer | SLC45A3-ELK4 | |
| --- | --- | --- |
| | Negative | positive |
| Negative | 4 | 2 |
| Positive | 2 | 6 |

Quantitative RT-PCR using TAQMAN technology. To quantify SLC45A3-ELK4 and endogenous ELK4 transcripts, custom designed primers and probes (SLC45A3-ELK4: primers in SLC45A3 exon 1 and ELK4 exon 2, probe in ELK4 exon 2) were employed in (ELK4, Hs00360812_m1) TAQMAN Gene Expression Assays (Applied Biosystems, Foster City, Calif.) for improved sensitivity and specificity of detection. The PCR reaction was prepared with TAQMAN RNA-to-CT™ 1-step Kit (Applied Biosystems) and 100 ng/well of total RNA in a final volume of 20 μl according to the manufacturers instructions and run on an ABI 7500 Fast Real-Time PCR System. Each target was run in triplicate and expression levels were calculated using the comparative $C_t$ method (ABI Bulletin 2, Applied Biosystems) with TCFL1 as a reference gene and given as fold change over the average expression levels of benign samples.

Example 4

Chromosome Rearrangement Did not Account for SLC45A3-ELK4 Expression

The development of a standard FISH break-apart assay requires using BACs which usually span 100-150 kb. The distance from SLC45A3 to ELK4 is 25 kb and thus was not suitable for detecting a possible deletion between these genes. Additionally, as seen in prior studies, including one by Wolf et al. (Neoplasia 2004; 6: 240-7), 1q is one of the most commonly deleted areas in prostate cancer making it less reliable for probes that widely flank the two genes. Therefore, it was reasoned that similar to the TMPRSS2-ERG fusion, where common deletion of the interstitial 3 mb chromosomal region separating TMPRSS2 and ERG occurs (Perner et al., Cancer Res 2006; 66: 8337-41), genomic loss within the 25 kb genomic region separating SLC45A3 and ELK4 cannot be explored. As described below primers were designed to amplify 13 loci on chromosome 1 that lie between SLC45A3 and ELK4 (FIG. 3a). The resulting amplicon raw data was normalized to a region on chromosome 1 (within ARHGEF) that is not altered from HapMap SNP data (McCarroll et al., Nat Genet 2008; 40: 1166-74). Indeed, deletion or partial deletion of this region was observed in several samples with both high (420_D and 1024_D) and low (38_A, 436_D and 25_T) SLC45A3-ELK4 transcript levels. The majority of samples were assessed as copy number neutral or demonstrated genomic gain in this region. This included 1 sample (427_A) with high levels of SLC45A3-ELK4 mRNA but copy number neutral and 1 sample (1701_A) that had low SLC45A3-ELK4 mRNA and high DNA amplification in this region. Taken together, a consistent loss of genomic DNA in cases with SLC45A3-ELK expression was not observed.

Chromosome 1q32, SLC45A3 to ELK4 region assessment. To assess the DNA copy number status of the of chromosome 1 region separating SLC45A3 and ELK4, primers were designed that targeted against repeat-masked genomic DNA to be used in a quantitative PCR (Q-PCR) assay that targeted 13 100-200 bp segments between the last exon of SLC45A3 and the first exon of ELK4. The primers were set forth in Table 2. Quantitation was performed using Q-PCR by relative standard curve method. Primers targeting a copy number stable chromosomal region in ARHGEF (chr1:155205397-155205600) were used for normalization (FWD: 5' TCTCTGCTCCCTCACTCTCAA 3' (SEQ ID NO: 35), REV: 5' TGTGCCTCTTCCATCGTTCT 3' (SEQ ID NO: 36). DNA from Hapmap sample NA12155 at 5 concentrations (0.5 ng-50 ng) was run for each of the 13 primer pairs to generate the standard curve per primer pair and per 384-well plate. All reactions were run in triplicates.

Example 5

Hormonal Treatment of LNCaP Cells Showed that SLC45A3-ELK4 was Androgen-Regulated This example presents results that demonstrate that over-expression of ELK4 upon androgen stimulation in LNCaP cells can result from over-expression of one or more SLC45A3-ELK4 fusion transcripts. The assay format used in these tests was adopted from Makkonnen et al. (*Oncogene* 2008; August 21; 27(36):4865-76. Epub 2008 May 12), who reported that ELK4 is a novel androgen receptor target in LNCaP cells. The assays performed repeated the experiments reported by Makkonnen et al. and included an assay for the SLC45A3-ELK4 transcript and, in addition, an assay for ELK4 that did not target the fusion transcript. At twelve hours following treatment with a synthetic androgen (R1881, 1 nM), a 25-fold induction of SLC45A3-ELK4 was observed, but no change was seen in ELK4 (FIG. 4a-4c). This induction was abrogated in the presence of the androgen antagonist Flutamide. As a control, the levels of KLK3 (PSA) mRNA were measured and a similar profile was observed. These results illustrate that over-expression of ELK4 upon androgen stimulation in LNCaP cells results from over-expression of SLC45A3-ELK4 fusion transcript.

Hormonal treatment of LNCaP. The prostate cancer cell line LNCaP was obtained from ATCC (Manassas, Va.; cat. # CRL-1740) and maintained according to the suppliers instructions. For hormonal treatment, cells were plated (500,000 cells/10 cm$^2$) in the presence of complete growth medium supplemented with 1% Penicillin/Streptomycin. Cells were starved for 48 h in charcoal-stripped (CS) medium (RPM-16401x, 5% CS-FBS, 1% Penicillin/Streptomycin) and then treated with R1881 (1 nM) or vehicle for 3 h, 12 h and 24 h. RNA was extracted using the TRIzol Reagent (Invitrogen, Carlsbad, Calif.), subjected to DNase treatment (DNA-free™ Kit, Applied Biosystems) according to the manufacturers instructions and used in quantitative RT-PCR with ETV1 (Hs00951947_m1) as an androgen read-out gene, specific to this cell line. To test for the specificity of androgen-stimulation cells were treated with 10 um Flutamide for 48 hours and then treated with R1881 as described above.

Summary of Experimental Results

This disclosure describes SLC45A3-ELK4 fusion transcripts that are expressed in benign prostate tissue and in prostate cancer. High levels of SLC45A3-ELK4 mRNA have been observed in a subset of prostate cancer samples, whereas no examples of benign tissue exhibited such high expression. Characterization of the fusion mRNA revealed a major variant in which SLC45A3 exon 1 is fused to ELK4 exon 2. Other minor variants include other downstream exons of both genes and one variant that included an 84-bp chromosome sequence that is located in an area separating the two genes. Due to the proximity of the two genes, Q-PCR probes were used to detect loss of DNA between the two genes. The results of the Q-PCR studies illustrate that, at least in some cases, no genomic rearrangement is needed for the SLC45A3-ELK4 transcripts to be produced. Indeed, high levels of SLC45A3-ELK4 transcript levels were found in a sample that was copy number neutral.

Chromosome 1q32.1 is a genetic region that is involved in chromosome loss and associated with prostate cancer (Wolf et al., *Neoplasia* 2004; 6: 240-7). Exon 1 of SLC45A3 is located roughly 50 Kb telomeric on 102.1 from ELK4 exon 2 and is transcribed in the same direction. A chromosome deletion of the interstitial region separating TMPRSS2 and ERG has been observed in 60% of TMPRSS2-ERG fusion prostate cancers (Pemer et al., *Cancer Res* 2006; 66: 8337-41). This disclosure presents data that shows that the expression of SLC45A3-ELK4 fusion transcript may result from a mechanism, called trans-splicing, that does not require a fusion of the SLC45A3 gene and the ELK4 gene.

Trans-splicing is believed to occur when exons from two separate pre-mRNAs are joined to create a single chimeric mRNA, which may occur between pre-mRNAs from the same gene (homotypic trans-splicing) or pre-mRNAs from different genes (intergenic trans-splicing). A delay in the transcription of two consecutive exons may promote trans-splicing of a transcript from a preceding exon to an exon from a different pre-mRNA. Genetic components that code for the SLC45A3-ELK4 fusion transcripts described herein include the first intron in SLC45A3 which is 15.5 kb long and which is separated from the ELK4 gene by an intergenic distance of about 25 kb. Although the utility of the compositions and methods described herein related to detection of SLC45A3-ELK4 fusion transcripts does not depend on any particular mechanism, a trans-splicing mechanism for creation of these fusion transcripts is supported by FISH analysis of ETS genes and known 5' fusion partners (Han et al. *Cancer Res* 2008; 68: 7629-37).

The high abundance of SLC45A4-ELK4 chimeric transcripts disclosed herein was unexpected. In prostate cancer cases with known TMPRSS2-ERG or SLC45A3-ERG fusions, there was no mutually exclusive expression observed between TMPRSS2-ERG and SLC45A3-ELK4 as seen with the other prostate cancer fusions (Tomlins et al., *Science* 2005; 310: 644-8). Interestingly, the 3 samples that yielded high SLC45A3-ELK4 transcript levels were negative for ERG rearrangement by FISH analysis.

SLC45A3 has been described as an organ specific marker for benign and malignant prostatic epithelial cells (Xu et al., *Am J Hum Genet* 2003; 72: 208-12), but its expression is diminished in metastatic prostate cancer (Yin et al., *Diagn Pathol* 2007; 2: 41). It is located on chromosome 1q32 directly neighbouring ELK4. ELK4 is a member of the ETS family of transcription factors and of the ternary complex factor (TCF) subfamily. Proteins of the TCF subfamily form a ternary complex by binding to the serum response factor and the serum response element in the promoter of the c-fos proto-oncogene. The protein encoded by this gene is phosphorylated by the kinases, MAPK1 and MAPK8.

ELK4 has been identified as an androgen receptor target gene in prostate cancer cells, in which induction of ELK4 mRNA variants upon androgen stimulation is most pronounced in metastatic, hormone-refractory prostate cancer (Makkonen et al., *Oncogene* 2008; August 21; 27(36):4865-76. Epub 2008 May 12). The results presented herein in the Examples of this disclosure confirm that ELK4 is over-expressed in prostate cancer, but only in a subset of tumors and only when it is fused to SLC45A3 genetic sequences that include a promoter. Examples disclosed herein describe TAQMAN assays that specifically detect SLC45A3-ELK4 mRNA and endogenous ELK4 mRNA. Only SLC45A3-ELK4 mRNA, and not endogenous ELK4 mRNA, was up-regulated upon treatment of LNCaP cells with R1881.

Thus, the changes in ELK4 expression described by Makkonen et al. (id.) were likely due to expression from SLC45A3-ELK4 fusions, rather than from wild type ELK4, because the results presented in this disclosure showed no androgen regulation of ELK4 in the absence of SLC45A3-ELK4 fusion transcripts.

Makkonen et al. (id.) also observed a retardation of prostate cancer cell growth (LNCaP), in vitro, following siRNA-mediated reduction of ELK4 mRNA. The data disclosed in Example 5 herein are consistent with SLC45A3-ELK4 fusion transcript expression as the primary target for siRNA inhibition.

TABLE 2

Primer Information for the quantitative PCR assay for chr1q32.1 (SEQ ID NOS: 9-36)

| Amplicon # | Location | Amplicon Length | | Primer (5'-3') | SEQ ID | Tm Value | GC % |
|---|---|---|---|---|---|---|---|
| 1 | chr1: 203872537 203872770 | 234 bp | F R | GTCCACGACTTCCAGCATTT TCAAACTCCACCCTTTCCAG | 9 10 | 60.1 60.1 | 50.0 50.0 |
| 5 | chr1: 203876382 203876617 | 236 bp | F R | CAACAAGACATTTTCAGTTAAGGGT GGCAAAACAAACAGGTATGCTATAA | 11 12 | 59.9 60.6 | 36.0 36.0 |
| 6 | chr1: 203876970 203877206 | 237 bp | F R | ACAGCTTTCCTTGCTCTCCA TGGCATCTGAAGAGGTTGAA | 13 14 | 60.1 59.4 | 50.0 45.0 |
| 8 | chr1: 203878442 203878658 | 217 bp | F R | ATTCCATCCTCAGCTAACAGGTAA CAAGGTGACAGTGTTTTGATGG | 15 16 | 60.4 60.4 | 41.7 45.5 |
| 9 | chr1: 203879147 203879339 | 193 bp | F R | CATACCCTTAGAGGTAGGTAACAGC AAGATGTGAATGGCAGTGGA | 17 18 | 58.8 59.1 | 48.0 45.0 |
| 10 | chr1: 203880053 203880262 | 210 bp | F R | CACACTGAAACAAAAGCCACA CTTTTGGGCAAGTGGACAAC | 19 20 | 59.8 60.5 | 42.9 50.0 |
| 11 | chr1: 203881426 203881651 | 226 bp | F R | GCCAGATAACCCAGGCTGTA GCCTTCATGCATTAGCCATT | 21 22 | 60.1 60.1 | 55.0 45.0 |
| 12 | chr1: 203882157 203882395 | 239 bp | F R | GTGCTGTTAGAAATAACTTTCCTGG GAGTTCTCAGTTTTCCCTGTGG | 23 24 | 59.6 60.2 | 40.0 50.0 |
| 13 | chr1: 203883436 203883641 | 206 bp | F R | TCCACACTCTTCACCCATCA CCTGTATGCTGAGCCTCATG | 25 26 | 60.1 59.4 | 50.0 55.0 |
| 14 | chr1: 203884232 203884442 | 211 bp | F R | TATTGGGTGCCAGAAAGTCC CTCCCTGCAGAGCCAGTTAC | 27 28 | 59.9 59.2 | 50.0 55.0 |
| 17 | chr1: 203891322 203891556 | 235 bp | F R | CCAACATGGGCAACATCTCT TGGGTTCAGGTGATGTCAGA | 29 30 | 60.9 60.1 | 50.0 50.0 |
| 18 | chr1: 203892750 203892972 | 223 bp | F R | CAAGCCCTTGCACAGGTTAT CATGGGAATAGGGAATGCAC | 31 32 | 60.1 60.2 | 50.0 50.0 |
| 19 | chr1: 203893840 203894055 (EXON #4 of | 216 bp | F R | AAACCGCACTTTGTGCTTCT CTTCAGGTCTCAACGGCTTC | 33 34 | 59.9 60.0 | 45.0 55.0 |
| Reference | chr1: 155205397 155205600 ARHGEF Introgenic | 204 bp | F R | TCTCTGCTCCCTCACTCTCAA TGTGCCTCTTCCATCGTTCT | 35 36 | 60.3 60.8 | 52.4 50.0 |

What is claimed is:

1. A method of detecting a fusion molecule associated with prostate cancer in a biological sample, comprising
providing a biological sample that contains nucleic acids,
adding a junction-specific oligonucleotide primer or probe to the sample, wherein such primer or probe hybridizes specifically to an SLC45A3-ELK4 junction in a fusion transcript representing a fusion between a 5' portion of a SLC45A3 mRNA and a 3' portion of an ELK4 mRNA, wherein the fusion transcript comprises a sequence selected from any one of SEQ ID NOS: 1-5, wherein the primer or probe is at least 14 nucleotides in length, and
detecting the level of the fusion transcript.

2. The method of claim 1, wherein said sample is selected from the group consisting of prostate tissue, blood, urine, semen, prostatic secretions and prostate cells.

3. The method of claim 1, wherein said sample is urine obtained from a patient following digital rectal exam.

* * * * *